United States Patent [19]

Ujihara

[11] Patent Number: 6,034,128
[45] Date of Patent: Mar. 7, 2000

[54] ESTER COMPOUNDS

[75] Inventor: Kazuya Ujihara, Yokohama, Japan

[73] Assignee: Sumitomo Chemical Company, Limited, Osaka, Japan

[21] Appl. No.: 09/323,132

[22] Filed: Jun. 1, 1999

[30] Foreign Application Priority Data

Jun. 9, 1998 [JP] Japan .................................. 10-160437

[51] Int. Cl.⁷ ........................... A01N 53/06; C07C 69/74; C07C 69/743
[52] U.S. Cl. ........................................... 514/531; 560/124
[58] Field of Search ............................. 560/124; 514/531

[56] References Cited

U.S. PATENT DOCUMENTS 4,219,565   8/1980   Roman .
4,281,183   7/1981   Roman .

*Primary Examiner*—Gary Geist
*Assistant Examiner*—Brian J. Davis
*Attorney, Agent, or Firm*—Stevens, Davis, Miller & Mosher, L.L.P.

[57] ABSTRACT

An ester compound represented by the formula:

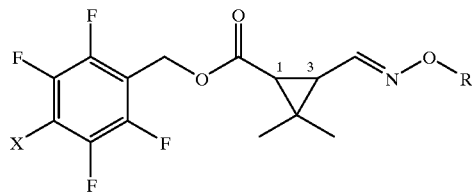

wherein R is a hydrogen atom, a $C_1$–$C_3$ alkyl group unsubstituted or substituted with one or more halogen atoms, an allyl group unsubstituted or substituted with one or more halogen atoms, or a propargyl group unsubstituted or substituted with one or more halogen atoms; and X is a hydrogen atom, a halogen atom, a $C_1$–$C_3$ alkyl group unsubstituted or substituted with one or more halogen atoms, a $C_2$–$C_3$ alkenyl group unsubstituted or substituted with one or more halogen atoms, a $C_2$–$C_3$ alkynyl group unsubstituted or substituted with one or more halogen atoms, a $C_1$–$C_3$ alkoxy group unsubstituted or substituted with one or more halogen atoms, a $C_1$–$C_3$ alkylthio group unsubstituted or substituted with one or more halogen atoms, or a $C_1$–$C_3$ alkoxymethyl group containing a $C_1$–$C_3$ alkoxy group unsubstituted or substituted with one or more halogen atoms, has an excellent pest-controlling effect.

14 Claims, No Drawings

ESTER COMPOUNDS

The present invention relates to an ester compound and a composition for controlling pest which contains said compound as an active ingredient.

BACKGROUND OF THE INVENTION

It has been known that some 2,2-dimethyl-3-(oxyiminomethyl)cyclopropanecarboxylic acid benzyl esters have an insecticidal and/or acaricidal activity (see U.S. Pat. No. 4,219,565).

The insecticidal and/or acaricidal activity of these compounds, however, is not sufficient in practice.

BRIEF SUMMARY OF THE INVENTION

In order to find a Compound having a sufficiently high pest-controlling effect, the present inventor earnestly investigated and consequently found that an ester compound represented by the general formula shown below has an excellent pest-controlling activity, whereby the present invention has been accomplished.

That is, the present invention provides an ester compound represented by the formula:

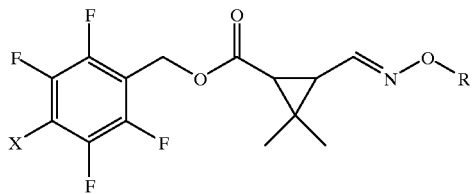

(2)

wherein R is a hydrogen atom, a $C_1$–$C_3$ alkyl group unsubstituted or substituted with one or more halogen atoms, an allyl group unsubstituted or substituted with one or more halogen atoms, or a propargyl group unsubstituted or substituted with one or more halogen atoms; and X is a hydrogen atom, a halogen atom, a $C_1$–$C_3$ alkyl group unsubstituted or substituted with one or more halogen atoms, a $C_2$–$C_3$ alkenyl group unsubstituted or substituted with one or more halogen atoms, a $C_2$–$C_3$ alkynyl group unsubstituted or substituted with one or more halogen atoms, a $C_1$–$C_3$ alkoxy group unsubstituted or substituted with one or more halogen atoms, a $C_1$–$C_3$ alkylthio group unsubstituted or substituted with one or more halogen atoms, or a $C_1$–$C_3$ alkoxymethyl group containing a $C_1$–$C_3$ alkoxy group unsubstituted or substituted with one or more halogen atoms (said ester compound is hereinafter referred to as the present compound); and a composition for controlling pest which contains the present compound as an active ingredient.

DETAILED DESCRIPTION OF THE INVENTION

In the present invention, the halogen atom includes fluorine atom, chlorine atom, bromine atom, etc. The $C_1$–$C_3$ alkyl group unsubstituted or substituted with one or more halogen atoms includes methyl group, ethyl group, trifluoromethyl group, etc. The allyl group unsubstituted or substituted with one or more halogen atoms includes allyl group, 2-chloroallyl group, 3-chloroallyl group, etc. The propargyl group unsubstituted or substituted with one or more halogen atoms includes propargyl group, 3-chloropropargyl group, 3-iodopropargyl group, etc. The $C_2$–$C_3$ alkenyl group unsubstituted or substituted with one or more halogen atoms includes allyl group, etc. The $C_2$–$C_3$ alkynyl group unsubstituted or substituted with one or more halogen atoms includes propargyl group, etc. The $C_1$–$C_3$ alkoxy group unsubstituted or substituted with one or more halogen atoms includes methoxy group, trifluoromethoxy group, etc. The $C_1$–$C_3$ alkylthio group unsubstituted or substituted with one or more halogen atoms includes methylthio group, etc. The $C_1$–$C_3$ alkoxymethyl group in which the $C_1$–$C_3$ alkoxy group is unsubstituted or substituted with one or more halogen atoms includes methoxymethyl group, etc.

The present compound can be produced, for example, by any of the following processes.

[Production Process A]

A process for producing the present compound by reacting a carboxylic acid compound of the formula:

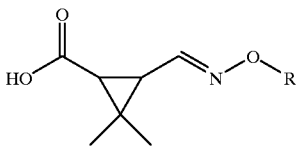

(3)

wherein R is as defined above, or its reactive derivative with an alcohol compound of the formula:

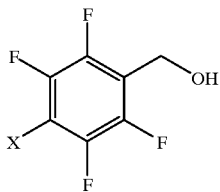

(4)

wherein X is as defined above, or its reactive derivative.

The reaction is usually carried out in an organic solvent optionally in the presence of a reaction assistant while removing by-products from the reaction system if necessary.

The reaction time ranges from 5 minutes to 72 hours. The reaction temperature ranges usually from –80° C. to the boiling point of the solvent used in the reaction or to +200° C.

The reactive derivative of the carboxylic acid compound of the formula (3) includes acid halides, acid anhydrides, $C_1$–$C_4$ alkyl esters, etc.

The reactive derivative of the alcohol compound of the formula (4) includes halides, sulfonic esters, quaternary ammonium salts, etc.

Although the molar ratio of the carboxylic acid compound of the formula (3) or its reactive derivative to the alcohol compound of the formula (4) or its reactive derivative can be arbitrarily determined, it is preferable to use them in equimolar or substantially equimolar amounts.

The reaction assistant includes, for example, tertiary amines such as triehylamine, 4-dimethylaminopyridine, diisopropylethylamine and the like; nitrogen-containing aromatic compounds such as pyridine and the like; organic bases such as alkali metal alkoxides (e.g., sodium methoxide and potassium tert-butoxide) and the like; inorganic bases such as sodium hydroxide, potassium carbonate, sodium hydride and the like; protonic acids such as p-toluenesulfonic acid, sulfuric acid and the like; Lewis acids such as titanium(IV) phenoxide and the like; dicyclohexylcarbodiimide; 1-ethyl-3-(3-dimnethylaminopropyl) carbodiimide hydrochloride; and a reagent consisting of diethyl azodicarboxylate and triphenylphosphine.

The reaction assistant is appripriately selected out of them, depending on the kind of the carboxylic acid compound of the formula (3) or its reactive derivative, and the alcohol compound of the formula (4) or its reactive derivative, which are to be subjected to the reaction. The amount of the reaction assistant used is appropriately selected depending on the mode of the reaction.

The solvent includes hydrocarbons such as benzene, toluene, hexane and the like; ethers such as diethyl ether, tetrahydrofuran and the like; halogenated hydrocarbons such as dichloromethane, 1,2-dichloroethane and the like; amides such as dimethylformamide and the like; ketones such as acetone and the like; organosulfur compounds such as dimethyl sulfoxide and the like; and mixtures thereof.

After completion of the reaction the reaction solution is subjected to conventional work-up procedures such as extraction with an organic solvent, concentration and the like to obtain the present compound. The present compound can be purified by operations such as chromatography, distillation, recrystallization and the like.

The carboxylic acid compound of the formula (3) or its reactive derivative can be produced according to the process disclosed in J. Chem. Soc. Perkin Trans. 1, 2470 (1970) or JP-A-54-160343. The alcohol compound of the formula (4) or its reactive derivative can be produced according to the process disclosed in JP-A-53-79845, JP-A-56-97251, JP-A-57-123146 or JP-A-61-207361. [Production process B]

A process for producing the present compound by reacting an aldehyde compound of the formula:

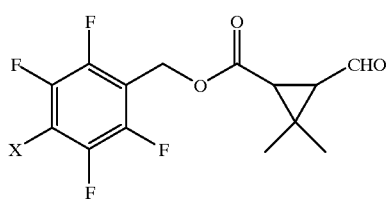

(5)

wherein X is as defined above, with a hydroxylamine compound of the formula:

RONH$_2$ (6)

wherein R is as defined above, or its protonic acid salt.

The reaction is usually carried out in a solvent optionally in the presence of a reaction assistant.

The reaction time ranges from 5 minutes to 72 hours. The reaction temperature ranges usually from −80° C. to the boiling point of the solvent used in the reaction or to +100° C.

The hydroxylamine compound of the formula (6) or its protonic acid salt is used in an amount ranging usually from 1 mole to excess moles, preferably from 1 mole to 5 moles, per mole of the aldehyde compound of the formula (5).

The protonic acid salt of the hydroxylamine compound includes, for example, hydrochloride and sulfate.

The reaction assistant optionally used includes, for example, tertiary amines such as triethylamine, 4-dimethylaminopyridine, diisopropylethylamine and the like; nitrogen-containing aromatic compounds such as pyridine and the like; organic bases such as alkali metal alkoxides (e.g., sodium methoxide) and organic acid salts (e.g., sodium acetate) and the like; and inorganic bases such as sodium hydroxide, potassium carbonate and the like.

The solvent includes hydrocarbons such as benzene, toluene, hexane and the like; ethers such as diethyl ether, tetrahydrofuran and the like; halogenated hydrocarbons such as dichloromethane, 1,2-dichloroethane and the like; amides such as dimethylformamide and the like; alcohols such as methanol and the like; organosulfur compounds such as dimethyl sulfoxide and the like; organic acids such as acetic acid and the like; water; and mixtures thereof.

After completion of the reaction the reaction solution is subjected to conventional work-up procedures such as extraction with an organic solvent, concentration and the like to obtain the present compound. The present compound can be purified by operations such as chromatography, distillation, recrystallization and the like.

The aldehyde compound of the formula (5) can be produced according to the process disclosed in JP-A-49-47531.

A present compound wherein R is not a hydrogen atom can be produced from a present compound wherein R is a hydrogen atom, for example, by the following process.
[Production process C]

A process for producing a present compound wherein R is not a hydrogen atom by reacting a present compound wherein R is a hydrogen atom with a compound of the formula:

R$^1$L (7)

wherein R$^1$ is a C$_1$–C$_3$ alkyl group unsubstituted or substituted with one or more halogen atoms, an allyl group unsubstituted or substituted with one or more halogen atoms, or a propargyl group unsubstituted or substituted with one or more halogen atoms; and L is a leaving group such as a halogen atom (e.g., chlorine atom, bromine atom and iodine atom), a substituted or unsubstituted alkylsulfonyloxy group (e.g., methanesulfonyloxy group and trifluoromethanesulfonyloxy group), a substituted or unsubstituted arylsulfonyloxy group (e.g., p-toluenesulfonyloxy group), a substituted or unsubstituted alkoxysulfonyloxy group (e.g., methoxysulfonyloxy group), a substituted ammonio group (e.g., trimethyl ammonio group), or a substituted iodonio group (e.g., phenyliocionio group).

The reaction is carried out usually in a solvent optionally in the presence of a reaction assistant.

The reaction time ranges from 5 minutes to 72 hours. The reaction temperature ranges usually from −80° C. to the boiling point of the solvent used in the reaction or to +100° C.

The compound of the formula (7) is used in an amount ranging usually from 1 mole to excess moles, preferably 1 mole to 5 moles, per mole of the present compound wherein R is a hydrogen atom.

The reaction assistant optionally used includes, for example, tertiary amines such as triethylamine, 4-dimethylaminopyridine, diisopropylethylamine and the like; nitrogen-containing aromatic compounds such as pyridine and the like; organic bases such as alkali metal alkoxides (e.g., potassium tert-butoxide) and organic acid salts (e.g., silver trifluoromethanesulfonate) and the like; and inorganic bases such as sodium hydroxide, potassium carbonate, sodium hydride and the like.

The solvent includes hydrocarbons such as benzene, toluene, hexane and the like; ethers such as diethyl ether, tetrahydrofuran and the like; halogenated hydrocarbons such as dichloromethane, 1,2-dichloroethane and the like; amides such as dimethylformamide and the like; ketones such as acetone and the like; organosulfur compounds such as dimethyl sulfoxide and the like; and mixtures thereof.

After completion of the reaction the reaction solution is subjected to conventional work-up procedures such as extraction with an organic solvent, concentration and the like to obtain the present compound wherein R is not a hydrogen atom. The compound can be purified by operations such as chromatography, distillation, recrystallization and the like.

The present compound has optical isomers (R, S) due to the asymmetric carbon atom, geometrical isomers (E, Z) due to the double bond, and geometrical isomers (cis, trans) due to the cyclopropane ring. The present invention encompasses all the optical isomers, geometical isomers and mixtures thereof having a pest-controlling activity.

The carboxylic acid compound of the formula (3) includes, for example, the following compounds:

3-methoxyiminomethyl-2,2-dimethylcyclopropanecarboxylic acid, and 3-ethoxyiminomethyl-2,2-dimethylcyclopropanecarboxylic acid.

The alcohol compound of the formula (4) includes, for example, the following compounds:

(2,3,5,6-tetrafluorophenyl)methanol, (2,3,4,5,6-pentafluorophenyl)methanol, (2,3,5,6-tetrafluoro-4-methylphenyl)methanol, and (2,3,5,6-tetrafluoro-4-methoxyphenyl)methanol.

The aldehyde compound of the formula (5) includes, for example, the following compounds:

(2,3,4,5,6-pentafluorophenyl)methyl 3-formyl-2,2-dimethylcyclopropanecarboxylate, (2,3,5,6-tetrafluco-4-methylphenyl)methyl 3-formyl-2,2-dimethylcyclopropanecarboxylate, and (2,3,5,6-tetrafluoro-4-methoxyphenyl)methyl 3-formyl-2,2-dimethylcyclopropanecarboxylate.

The hydroxylamine compound of the formula (6) includes, for example, the following compounds:

hydroxylamine,

O-methylhydroxylamine, and

O-ethylhydroxylamine.

The compound of thus formula (7) includes, for example, the following compounds:

methyl chloride, ethyl bromide, methyl iodide, methyl methanesulfonate, methyl p-toluenesulfonate, and dimethylsulfuric acid.

The insect pests (injurious insects and injurious acarines) on which the present compound has a controlling effect include, for example, the following:

Hemiptera

Delphacidae (planthoppers) such as *Laodelphax striatellus* (small brown planthopper), *Nilaparvata lugens* (brown planthopper) and *Sogatella furcifera* (white-backed rice planthopper); Deltocephalidae (leaf-hoppers) such as *Nephotettix cincticeps* (green rice leafhopper) and *Nephotettix virescens* (green rice leafhopper); Aphididae (aphids); Pentatomidae (bugs); Aleyrodidae (whiteflies); Coccidae (scales); Tingidae (lace bugs); Psyllidae (psyllids); etc.

Lepidoptera

Pyralidae (pyralid moths) such as *Chilo suppressalis* (rice stem borer), *Cnaphalocrocis medinalis* (rice leafroller) and *Plodia interpunctella* (Indian meal moth); Noctuidae such as *Spodoptera litura* (tobacco cutworm), *Pseudaletia separata* (rice armyworm) and *Mamestra brassicae* (cabbage armyworm); Pieridae such as *Pieris rapae crucivora* (common cabbageworm); Tortricidae (tortricid moths) such as Adoxophyes spp.; Carposinidae; Lyonetiidae (lyonetiid moths); Lymantriidae (tussock moths); Antographa spp.; Agrotis spp. such as *Agrotis segetum* (turnip cutworm) and *Agrotis ipsilon* (black cutworm); Helicoverpa spp.; Heliothis spp.; *Plutella xylostella* (diamondback moth); *Parnara guttata* (rice skipper); *Tinea pellionella* (casemaking clothes moth); *Tineola bisselliella* (webbing clothes moth); etc.

Diptera

Culex spp. such as *Culex pipiens pallens* (common mosquito) and *Culex tritaeniorhynchus*; Aedes spp. such as *Aedes aegypti* and *Aedes albopictus*; Anopheles spp. such as *Anopheles sinensis*; Chironomidae midges; Muscidae such as *Musca domestica* (housefly), *Muscina stabulans* (false stablefly); Calliphoridae; Sarcophagidae; Anthomyiidae (anthomylid flies) such as *Delia platura* (seedcorn maggot), *Fannia canicularis* (little housefly); and *Delia antiqua* (onion maggot); Tephritidae (fruit flies); Drosophilidae (small fruit flies, vinegar flies); Psychodidae (moth flies, sand flies); Simuliidae (black flies); Tabanidae; Stomoxyidae (stable flies); biting midges; etc.

Coleoptera corn rootworms such as *Diabrotica virgifera* (western corn rootworm) and *Diabrotica undecimpunctaca* howardi (southern corn rootwdrm); Scarabaeidae (scarabs) such as *Anomala cuprea* (cupreous chafer) and *Anomala rufocuprea* (soybean beatle); Curculionidae (weevils) such as *Sitophilus zeamais* (maize weevil), *Lissorhoptrus oryzophilus* (ricewater weevil), *Anthonomus grandis grandis* (boll weevil) and *Callosobruchus chinensis* (adzuki bean weevil); Tenebr:onidae (darkling beetles) such as *Tenebrio molitor* (yellow mealworm) and *Tribolium castaneum* (red fluor beetle); Chrysomelidae (corn rootworms) such as *Oulema oryzae* (rice leaf beetle), *Phyllotreta striolata* (striped flea beetles) and *Aulacophora femoralis* (cucurbit leaf beetle); Anobiidae; Epilachna spp. such as *Henosepilachna vigintioctopunctata* (twenty-eight-spotted ladybirds); Lyctidae (powder post beetles); Bostrychidae (false powder post beetles); Cerambycidae; Paederus fuscipes (robe beetle); etc.

Dictyoptera

*Blattella germania* (German cockroach), *Periplaneta fuliginosa* (smokybrown cockroach), *Periplaneta americana* (American cockroach), *Periplaneta brunnea* (brown cockroach), *Blatta orientalis* (oriental cockroach), etc.

Thysanoptera (thrips)

*Thrips palmi*, *Thrips hawailensis* (flower thrips), *Frankliniella occidentalis* (western flower thrips), etc.

Hymenoptera

Formicidae (ants); Vespidae (hornets); Bethylidae (bethylid wasps); Tenthredinidae (sawflies) such as *Athalia rosae ruficornis* (cabbage sawfly); etc.

Orthoptera

Gryllotalpidae (mole crickets), Acrididae (grasshoppers), etc.

Siphonaptera

*Ctenocephalides caris, Ctenocephalides felis, Pulex irritans*, etc.

Anoplura

*Pediculus humanus, Phthirus pubis*, etc.

Isoptera termites

*Reticulitermes speratus, Coptotermes formosanus* (Formosan subterranean termite), etc.

Acarina (mites and ticks)

Pyroglyphidae such as *Dermatophagoides farinae* and *Dermatophagoides pteronyssnus*; Acaridae such as *Tyrophagus putrescentiae* Schrank (mold mite, copra mite, forage mite) and *Aleuroglyphus ovatus* Troupeau (brown legged grain mite); Glycyphagidae such as *Glycyphagus privatus, Glycyphagus domesticus* and *Glycyphagus destructor* Schrank (groceries mite); Cheyletidae such as *Cheyletus melaccensis* and *Cheyletus moorei*; Tarsonemidae; Chrtoglyphus; Oribatei; Tetranychidae (spider mites) such as Tetranychus urticae (two-spotted spider mite), *Tetranychus kanzawai* (Kanzawa spider mite), *Panonychus citri* (citrus red mite) and *Panonychus ulmi* (European red mite); Ixodidae such as *Haemaphysalis longicornis*; etc.

The present compound is effective also against insect pests resistant to the existing agents for controlling insects and/or acarines.

The composition for controlling pest according to the present invention is intended for, for example, killing and repelling pests.

When the present compound is used as an active ingredient of the composition for controlling pest, the present compound is applied usually after having been formulated into various formulations, for example, oil formulations; emulsifiable concentrates; wettable powders; flowable concentrates (e.g., aqueous suspension concentrates and aqueous emulsion concentrates); granules; dusts; aerosols; heating fumigants (e.g., mosquito coils, electric mosquito mats, and solutions for heating fumigation using an absorbent wick); heating smoking formulations (e.g., self-burning-type smoking formulations, chemical-reaction-type smoking formulations, and electrically heating-type smoking formulations using a porous ceramic plate); non-heating volatile formulations (e.g., resin volatile formulations, and impregnated paper volatile formulations); foggings; ULV formulations; poisonous baits; or the like, either by mixing the present compound with a solid carrier, liquid carrier, gaseous carrier or bait, or by impregnating a base material such as a mosquito coil or mat with the present compound, and optionally adding a surfactant or other auxiliaries for formulation.

These formulations usually contain the present compound as an active ingredient in an amount of 0.001 to 95% by weight.

The solid carrier used for formulation includes, for example, fine powders and granules of clays (e.g. kaolin clay, diatomaceous earth, synthetic hydrated silicon dioxide, bentonite, fubasami clay and acid clay), talcs, ceramics, and other inorganic minerals (e.g. sericite, quartz, activated carbon, calcium carbonate and hydrated silica), and chemical fertilizers (e.g. ammonium sulfate, ammonium phosphate, ammonium nitrate, urea and ammonium chloride). The liquid carrier includes, for example, water, alcohols (e.g., methanol and ethanol), ketones (e.g., acetone and methyl ethyl ketone), aromatic hydrocarbons (e.g., benzene, toluene, xylene, ethylbenzene and methylnaphthalene), aliphatic hydrocarbons (e.g., hexane, cyclohexane, kerosene and light oil), esters (e.g., ethyl acetate and butyl acetate), nitriles (e.g., acetonitrile and isobutyronitrile), ethers (e.g., diisopropyl ether and dioxane), acid amides (e.g., N,N-dimethylformamide and N,N-dimethylacetamide), halogenated hydrocarbons (e.g., dichloromethane, trichloroethane and carbon tetrachloride), dimethyl sulfoxide, and vegetable oils (e.g., soybean oil and cotton seed oil). The gaseous carrier, i.e., propellant, includes, for example, CFC gas, butane gas, LPG (liquefied petroleum gas, dimethyl ether and carbon dioxide.

The surfactant includes, for example, alkyl sulfates, alkylsulfonates, alkylarylsulfonates, alkyl aryl ethers and their polyoxyethylenated products, polyethylene glycol ethers, polyhydric alcohol esters and sugar alcohol derivatives.

The auxiliaries for formulation such as adhesive agents and dispersants include, for example, casein, gelatin, polysaccharides (e.g. starch powder, gum arabic, cellulose derivatives and alginic acid), lignin derivatives, bentonite, saccharides, and synthetic water-soluble polymers [e.g. poly (vinyl alcohol)s, poly(vinylpyrrolicone)s and poly(acrylic acid)s]. The stabilizer includes, for example, PAP (acidic isopropyl phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils, surfactants, and fatty acids or their esters.

The base material for poisonous bait includes, for example, bait components (e.g. cereal flour, vegetable oils, saccharides and crystalline cellulose), antioxidants (e.g., dibutylhydroxytoluene and nordihydroguaiaretic acid), preservatives (e.g., dehydroacetic acid), agents for preventing consumption by children or pets (e.g., red pepper powder) and attractants (e.g., cheese perfume, onion perfume and peanut oil).

The formulation into a flowable concentrate (an aqueous suspension concentrate or an aqueous emulsion concentrate) can be carried out generally by finely dispersing 1 to 75% of the present compound in water containing 0.5 to 15% of a dispersant, 0.1 to 10% of a suspension assistant (e.g., a protective colloid or a compound capable of imparting thixotropic properties) and 0 to 10% of suitable auxiliaries (e.g., defoaming agents, rust preventives, stabilizers, spreaders, penetration assistants, anti-freezing agents, bactericides, and fungicides). It is also possible to prepare an oil-based suspension concentrate by using, in place of water, an oil substantially incapable of dissolving the present compound.

The protective colloid includes, for example, gelatin, casein, gums, cellulose ether and poly(vinyl alcohol)s.

The compound capable of imparting thixotropic properties includes, for example, bentonite, aluminum magnesium silicate, xanthan gum and poly(acrylic acid)s.

The formulations thus obtained are applied as they are or after dilution with water or the like. It is also possible to apply them in admixture or combination with other insecticides, acaricides, nematicides, soil insect pest controllers, fungicides, herbicides, plant growth regulators, repellents, synergists, fertilizers, or soil conditioners.

The insecticides, nematicides, acaricides and soil insect pest controllers include, for example, organophosphorus compounds such as Fenitrothion [O,O-dimethyl O-(3-methyl-4-nitrophenyl)phosphorothioate], Fenthion [O,O-dimethyl O-(3-methyl-4-(methylthio)-phenyl) phosphorothioate], Diazinon [O,O-diethyl O-2-isopropyl-6-methylpyrimidin-4-yl phosphorothioate], Chlorpyrifos [O,O-diethyl O-3,5,6-trichloro-2-pyridyl phosphorothioate], Acephate [O,S-dimethyl acetyl-phosphoramidothioate], Methiciathion [S-2,3-dihydro-5-methoxy-2-oxo-1,3,4-thiadiazol-3-ylmethyl O,O-dimethyl phosphorodithioate], Disulfoton [O,O-diethyl S-2-ethylthioethyl phosphorodithioate], Dichlorvos [2,2-dichlorovinyl dimethyl phosphate], Sulprofos [O-ethyl O-4-(methylthio) phenyl S-propyl phosphorodithioate], Cyanophos [O-4- cyanophenyl O,O-dimethyl phosphorothioate], Dioxabenzcphos [2-methoxy-4H-1,3,2-benzodioxaphosphorine-2-sulfide], Dimethoate [O,O-dimethyl S-(N-methylcarbamoylmethyl) dithiophosphate], Phenthoate [ethyl 2-dimethoxyphosphinothioylthio-(phenyl)acetate], Malathion [diethyl (dimethoxyphosphinothioylthio)succinate], Trichlorfon [dimethyl 2,2,2-trichloro-1-hydroxyethylphosphonate], Azinphosmethyl [S-3,4-dihydro-4-oxo-1,2,3-benzotriazin-3-ylmethyl O,O-dimethylphosphorodithioate], Monocrotophos [dimethyl {(E)-1-methyl-2-(methylcarbamoyl)vinyl}phosphate], Ethion [O,O,O',O '-tetraethyl-S,S'-methylenebis (phosphorodithioate)] and the like; carbamate compounds such as BPMC [2-sec-butylphenyl methylcarbamate], Benfuracarb [ethyl N-{2,3-dihydro-2,2-dimethylbenzofuran-7-yloxycarbonyl (methyl)-aminothio}-N-isopropyl-β-alaninate], Propoxur [2-isopropoxyphenyl-N-methylcarbamate], Carbosulfan [2,3-dihydro-2,2-dimethyl-7-benzo [b] furanyl N-dibutyl-aminothio-N-methylcarbamate], Carbaryl [1-naphthyl N-methylcarbamate], Methomyl [S-methyl-N-(methylcarbamoyloxy)thioacetimidate], Ethiofencarb [2-(ethylthiomethyl)phenyl methylcarbamate], Aldicarb [2-methyl-2-(methylthio)propionaldehyde O-methycarbamoyloxime], Oxamyl [N,N-dimethyl-2-methylcarbamoyloxyimino-2-(methylthio)acetamide], Fenothiocarb [S-4-phenoxybutyl N,N-dimethylthiocarbamate] and the like; pyrethroid compounds such as Etofenprox [2-(4-ethoxyphenyl)-2-methyl-1-(3-phenoxybenzyl)oxypropane], Fenvalerate [(RS)-α-cyano-3-phenoxybenzyl (RS)-2-(4-chlorophenyl)-3-methylbutyrate], Esfenvalerate [(S)-α-cyano- 3-phenoxybenzyl (S)-2-(4-chlorophenyl)-3-methylbutyrate], Fenpropathrin [(RS)-α-cyano-3-phenoxybenzyl 2,2,3,3-tetramethylcyclopropanecarboxylate], Cypermethrin [(RS)-α-cyano-3-phenoxybenzyl (1RS)-cis,trans-3-(2,2-dichlorovinyl)-2,2-dimethylcyclopropanecarboxylate], Permethrin [3-phenoxybenzyl (1RS)-cis,trans-3-(2,2-dichlorovinyl)-2,2-dimethylcyclopropanecarboxylate], Cyhalothrin [(RS)-α-cyano-3-phenoxybenzyl (1RS,3Z)-cis-3-(2-chloro-3,3,3-trifluoroprop-1-enyl)-2,2-dimethylcyclopropanecarboxylate], Deltamethrin [(S)-α-cyano-3-phenoxybenzyl (1R)-cis-3-(2,2-dibromovinyl)-2,2-dimethylcyclopropanecarboxylate], Cycloprothrin [(RS)-α-cyano-3-phenoxybenzyl (RS)-2,2-dichloro-1-(4-ethoxyphenyl)cyclopropanecarboxylate], Fluvalinate [α-cyano-3-phenoxybenzyl N-(2-chloro-α, α, α-trifluoro-p-tolyl)-D-valinate], Bifenthrin [2-methyl-3-phenylbenzyl (1RS,3Z)-cis-3-(2-chloro-3,3,3-trifluoro-1-propenyl)-2,2-dimethylcyclopropanecarboxylate], Halfenprox [2-(4-bromodifluoromethoxyphenyl)-2-methyl-1-(3-phenoxybenzyl)oxypropane], Tralomethrin [(S)-α-cyano-3-phenoxybenzyl (1R)-cis-3-(1,2,2,2-tetrabromoethyl)-2,2-dimethylcyclopropanecarboxylate], Silafluofen [(4-ethoxyphenyl)- {3-(4-fluoro-3-phenoxyphenyl)propyl} dimethylsilane], d-Phenothrin [3-phenoxybenzyl (1R)-cis,trans-2,2-dimethyl-3-(2-methyl-1-propenyl) cyclopropanecarboxylate], Cyphenothrin [(RS)-α-cyano-3-phenoxybenzyl (1R)-cis,trans-2,2-dimethyl-3-(2-methyl-1-propenyl)cyclopropanecarboxylate], d-Resmethrin [5-benzyl-3-furylmethyl (1R)-cis,trans-2,2-dimethyl-3-(2-methyl-1-propenyl)cyclopropanecarboxylate], Acrinathrin [(S)-α-cyano-3-phenoxybenzyl (1R,3Z)-cis-(2,2-dimethyl-3- {3-oxo-3-(1,1,1,3,3,3-hexafluoro-propyloxy)propenyl} cyclopropanecarboxylate], Cyfluthrin [(RS)-α-cyano-4-fluoro-3-phenoxybenzyl 3-(2,2-dichlorovinyl)-2,2-dimethylcyclopropanecarboxylate], Tefluthrin [2,3,5,6-tetrafluoro-4-methylbenzyl (1RS,3Z)-cis-3-(2-chloro-3,3,3-trifluoro-1-propenyl)-2,2-dimethylcyclopropanecarboxylate], Transfluthrin [2,3,5,6-tetrafluorobenzyl (1R)-trans-3-(2,2-dichlorovinyl)-2,2-dimethylcyclopropaecarboxylate], Tetramethrin [3,4,5,6-tetrahydrophthalimidomethyl (1RS)-cis,trans-2,2-dimethyl-3-(2-methyl-1-propenyl)cyclopropanecarboxylate], Allethrin [(RS)-2-methyl-4-oxo-3-(2-propenyl)-2-cyclopenten-1-yl (1RS)-cis,trans-2,2-dimethyl-3-(2-methyl-1-propenyl)cyclopropanecarboxylate], Prallethrin [(S)-2-methyl-4-oxo-3-(2-propynyl)-2-cyclopenten-1-yl (1R)-cis, trans-2,2-dimethyl-3-(2-methyl-1-propenyl) cyclopropanecarboxylate], Empenthrin [(RS)-1-ethynyl-2-methyl-2-pentenyl (1R)-cis,trans-2,2-dimethyl-3-(2-methyl-1-propenyl)cyclopropanecarboxylate], Imiprothrin [2,5-dioxo-3-(2-propynyl)imidazolidin-1-ylmethyl (1R)-cis,trans-2,2-dimethyl-3-(2-methyl-1-propenyl) cyclopropanecarboxylate], d-Flamethrin [5-(2-propynyl) furfuryl (1R)-cis,trans-2,2-dimethyl-3-(2-methyl-1-propenyl)cyclopropanecarboxylate], 5-( 2-propynyl)furfuryl 2,2,3,3-tetramethylcyclopropanecarboxylate] and the like; thiadiazine derivatives such as Buprofezin [2-tert-butylimino-3-isopropyl-5-phenyl-1,3,5-thiadiazin-4-one] and the like; Nitroimidazolidine derivatives such as Imidacloprid [1-(6-chloro-3-pyridylmethyl)-N-nitroimidazolidin-2-ylideneamine] and the like; nereistoxin derivatives such as Cartap [S,S'-(2-dimethylaminotrimethylene)bis (thiocarbamate)],

[N,N-dimethyl-1,2,3-trithian-5-ylamine],

[S,S'-2-dimethylaminotrimethylenedi-(benzenethiosulfonate)] and the like; N-cyanoamidine derivatives such as N-cyano-N'-methyl-N'-(6-chloro-3-pyridylmethyl)acetoamidine and the like; chlorinated hydrocarbon compounds such as Endosulfan [6,7,8,9,10,10-hexachloro-1,5,5a,6,9,9a-hexahydro-6,9-methano-2,4,3-benzodioxathiepin 3-oxide], γ-BHC [1,2,3,4,5,6-hexachlorocyclohexane], Dicofol [1,1-bis (4-chlorophenyl)-2,2,2-trichloroethanol] and the like; benzoylphenylurea compounds such as Chlorfluazuron [1-{3,5-dichloro-4-(3-chloro-5-trifluoromethylpyridin-2-yloxy)phenyl}-3-(2,6-difluorobenzoyl)urea], Teflubenzuron [1-(3,5-dichloro-2,4-difluorophenyl)-3-(2,6-difluorobenzoyl)urea], Flufenoxuron [1-{4-(2-chloro-4-trifluoromethylphenoxy)-2-fluorophenyl}-3-(2,6-difluorobenzoyl)urea] and the like; formamidine derivatives such as Amitraz [N,N'-{(methylimino)-dimethylidine }-di-2,4-xylidine], Chlordimeform [N'-(4-chloro-2-methylphenyl)-N,N-dimethylmethinimidamide] and the like; thiourea derivatives such as Diafenthiuron [N-(2,6-diisopropyl-4-phenoxyphenyl)-N'-t-butylthiourea] and the like; N-phenylpyrazole compounds; Metoxadiazon [5-methoxy-3-(2-methoxyphenyl)-1,3,4-oxadiazol-2-(3H)-one]; Bromopropylate [isopropyl 4,4'-dibromobenzilate]; Tetradifon [4-chlorophenyl 2,4,5-trichlorophenyl sulfone]; Quinomethionate [S,S-6-methylquinoxaline-2,3-diyldithiocarbonate]; Propargite [2-(4-tert-butylphenoxy)cyclohexylprop-2-yl sulfite]; Fenbutatin oxide [bis {tris(2-methyl-2-phenylpropyl)tin} oxide]; Hexythiazox [(4RS,5RS)-5-(4-chlorophenyl)-N-cyclohexyl-4-methyl-2-oxo-1,3-thiazolidine-3-carboxamide];

[3,6-bis(2-chlorophenyl)-1,2,4,5-tetrazine]; Pyridaben [2-tert-butyl-5-(4-tert-butylbenzylthio)-4-chloropyridazin-3(2H)-one]; Fenpyroximate [tert-butyl (E)-4-[(1,3-dimethyl-5-phenoxypyrazol-4-yl) methyleneaminooxymethyl]benzoate]; Tebufenpyrad

[N-4-tert-butylbenzyl)-4-chloro-3-ethyl-1-methyl-5-pyrazolecarboxamide]; Polynactin complexes [tetranactin, dinactin and trinactin]; Pyrimidifen [5-chloro-N-[2-{4-(2-ethoxyethyl)-2,3-dimethylphenoxy}-ethyl]-6-ethylpyrimidin-4-amine]; Milbemectin; Abamectin; ivermectin; azadirachtin [AZAD], etc. The repellents include, for example, 3,4-caranediol, N,N-diethyl-m-toluamide, 1-methylpropyl 2-(2-hydroxyethyl)-1-piperidinecarboxylate, p-menthane-3,8-diol, and plant essential oils such as hyssop oil. The synergists include, for example, bis-(2,3,3,3-tetrachloropropyl) ether (S-421), N-(2-ethylhexyl)bicyclo[2.2.1]hept-5-ene-2,3-dicarboximide (MGK-264), and α-[2-(2-butoxyethoxy)-ethoxy]-4,5-methylenedioxy-2-propyltoluene (piperonyl butoxide).

When the present compound is used as an active ingredient of a composition for controlling pest, it is usually applied in a dosage ranging from 5 to 500 g per 10 ares. When it is used in the form of emulsifiable concentrates, wettable powders or flowable concentrates, it is applied after having been diluted with water so that the formulations have a concentration of the present compound falling within the range of from 0.1 to 1,000 ppm. When the present compound is used in the form of granules, dusts or resin formulations, these formulations are applied as they are without dilution. When the present compound is used as an active ingredient of a composition for controlling pest for preventing domestic epidemics or for controlling pest for animals, formulations in the form of emulsifiable concentrates, wettable powders or flowable concentrates are applied usually after having been diluted with water so that the formulations have a concentration of the present compound falling within the range of from 0.1 to 10,000 ppm. Formulations in the form of oil formulations, aerosols, fumigants, smoking formulations, volatile formulations, foggings, ULV formulations, poisonous baits or resin formulations are applied as they are.

Both the applying dosage and the applying concentration of the above formulations can be properly determined depending on the conditions such as the type of formulation, when, where and how these formulations are applied, kind of pests, degree of damage, etc., and can be increased or decreased irrespective of the above range.

EXAMPLES

The present invention is illustrated with reference to the following production example, formulation examples and test examples, which should not be construed as limiting the scope of the invention.

Firstly, production of the present compound is exemplified. In the production examples, the numbers of the present compounds are those shown in Tables 1 to 16 below.

Production Example 1

2.06 Grams of (1R)-trans-2,2-dimethyl-3-(2-methyl-1-propenyl)cyclopropanecarboxylic acid chloride was added to a mixture of 1.78 g of (2,3,5,6-tetrafluoro-4-methylphenyl)methanol, 0.87 g of pyridine and 20 ml of tetrahydrofuran under ice-cooling. The resulting mixture was stirred at room temperature for 8 hours. The reaction mixture was poured into about 100 ml of ice water and extracted twice with 100 ml of ethyl acetate. The combined ethyl acetate layer was washed with a saturated aqueous sodium chloride solution, dried over anhydrous sodium sulfate and then concentrated under reduced pressure. The residue was purified by a silica gel column chromatography (eluent: hexane/ethyl acetate=20/1) to obtain 2.75 g (yield: 87%) of (2,3,5,6-tetrafluoro-4-methylphenyl)methyl (1R)-trans-2,2-dimethyl-3-(2-methyl-1-propenyl) cyclopropanecarboxylate.

A mixture of 1.27 g of (2,3,5,6-tetrafluoro-4-methylphenyl)methyl (1R)-trans-2,2-dimethyl-3-(2-methyl-1-propenyl)cyclopropanecarboxylate, 20 ml of methanol and 20 ml of ethyl acetate was cooled to −78° C. Oxygen-containing ozone was bubbled into the mixture while stirring until the reaction mixture was colored blue. Then, nitrogen gas was bubbled into the blue reaction mixture to remove the excess ozone. Thereafter, 5 ml of dimethyl sulfide was added thereto. The resulting mixture was heated to room temperature. The reaction mixture, after having been allowed to stand for one day, was concentrated under reduced pressure. 20 Milliliters of acetone, 2 ml of water and 0.2 g of p-toluenesulfonic acid monohydrate were added to the resultant residue. The resulting reaction mixture, after having been allowed to stand at room temperature for 2 hours, was poured into water and extracted with diethyl ether. The organic layer was dried over anhydrous sodium sulfate and then concentrated under reduced pressure. The resultant residue was purified by a silica gel column chromatography (eluent: hexane/ethyl acetate=10/1) to obtain 0.98 g (yield: 82%) of (2,3,5,6-tetrafluoro-4-methylphenyl)methyl (1R)-trans-3-formyl-2,2-dimethyl-cyclopropanecarboxylate, m.p. 43.2° C.

A mixture of 0.32 g of O-methylhydroxylamine hydrochloride, 0.16 g of sodium hydroxide and 10 ml of methanol was stirred for 1 hour. To the stirred mixture, a solution of 0.56 g of (2,3,5,6-tetrafluoro-4-methylphenyl) methyl (1R)-trans-3-formyl-2,2-dimethyl-cyclopropanecarboxylate in 3 ml of methanol was added. After 12 hours of stirring, water was added to the reaction mixture, which was when extracted with diethyl ether. The organic layer was dried over sodium sulfate and then concentrated under reduced pressure. The resultant residue was purified by a silica gel column chromatography using a 10:1 mixture of hexane and ethyl acetate as an eluent, to obtain 0.28 g (yield: 46%) of (2,3,5,6-tetrafluoro-4-methylphenyl) methyl (1R)-trans-3-((E)-methoxyiminomethyl)-2,2-dimethylcyclopropanecarboxylate (present compound 11). The chromatography was continued while replacing the eluent with a 4:1 mixture of hexane and ethyl acetate, to obtain 0.23 g (yield: 38%) of (2,3,5,6-tetrafluoro-4-methylphenyl)methyl (1R)-trans-3-((Z)-methoxyiminomethyl)-2,2-dimethylcyclopropanecarboxylate (present compound 36).

Production Example 2

2.4 Grams of a 40% solution of diisopropyl azodicarboxylate in toluene was added to a mixture of 0.63 g of a 1:1 mixture of (1R)-trans-3-((E)-methoxyimino)-2,2-dimethylcyclopropanecarboxylic acid and (1R)-trans-3-((Z)-methoxyimino)-2,2-dimethylcyclo-propanecarboxylic acid, 0.78 g of (2,3,5,6-tetrafluorophenyl)methanol, 1.16 g of triphenylphosphine and 15 ml of tetrahydrofuran while stirring. The reaction mixture, after having been allowed to stand for one day, was concentrated under reduced pressure. The resultant residue was subjected to a silica gel column chromatography (eluent: hexane/ethyl acetate=3/1). The obtained fraction was subjected again to a silica gel column chromatography (eluent: hexane/ethyl acetate=10/1) to obtain 0.53 g (yield: 42%) of (2,3,5,6-tetrafluorophenyl) methyl (1R)-trans-3-((E)-methoxy-iminomethyl)-2,2-dimethylcyclopropanecarboxylate (present compound 9)

followed by 0.47 g (yield: 37%) of (2,3,5,6-tetrafluorophenyl)methyl (1R)-trans-3-((Z)-methoxyiminomethyl)-2,2-dimethylcyclopropanecarboxylate (present compound 34).

Production Example 3

0.81 Grams of 1:1 mixture of (1R)-cis-3-((E)-methoxyimino)-2,2-dimethylcyclopropanecarboxylic acid and (1R)-cis-3-((Z)-methoxyimino)-2,2-dimethylcyclopropanecarboxylic acid, 1.01 g of 1-(chloromethyl)-2,3,5,6-tetrafluoro-4-methylbenzene, 1.1 g of triethylamine and 15 ml of N,N-dimethylformamide were mixed. The resulting mixture was stirred at 80° C. for 3 hours. The reaction mixture was cooled to room temperature, water was added thereto, and then extracted with tert-butyl methyl ether. The organic layer was dried over sodium sulfate, and then concentrated under reduced pressure. The resultant residue was subjected to a silica gel column chromatography (eluent: hexane/ethyl acetate=10/1) to obtain a 1:1 mixture of (2,3,5,6-tetrafluoro-4-methylphenyl)methyl (1R)-cis-3-((E)-methoxyiminomethyl)-2,2-dimethylcyclopropanecarboxylate (present compound 61) and (2,3,5,6-tetrafluoro-4-methylphenyl)methyl (1R)-cis-3-((Z)-methoxyiminomethyl)-2,2-dimethylcyclopropanecarbDxylate (present compound 86) in a yield of 82%.

Examples of the present compounds of the formula (2) are given in Tables 1 to 16 together with compound numbers; however, they are not intended in any way to limit the present compounds thereto.

TABLE 1

| Compound No. | R | X | Configuration of acid component |
|---|---|---|---|
| 1 | H | H | 1R-trans-E |
| 2 | H | F | 1R-trans-E |
| 3 | H | Me | 1R-trans-E |
| 4 | H | allyl | 1R-trans-E |
| 5 | H | propargyl | 1R-trans-E |
| 6 | H | MeOCH$_2$ | 1R-trans-E |
| 7 | H | MeO | 1R-trans-E |
| 8 | H | MeS | 1R-trans-E |
| 9 | Me | H | 1R-trans-E |
| 10 | Me | F | 1R-trans-E |
| 11 | Me | Me | 1R-trans-E |
| 12 | Me | allyl | 1R-trans-E |
| 13 | Me | propargyl | 1R-trans-E |
| 14 | Me | MeOCH$_2$ | 1R-trans-E |
| 15 | Me | MeO | 1R-trans-E |
| 16 | Me | MeS | 1R-trans-E |
| 17 | Et | H | 1R-trans-E |
| 18 | Et | Me | 1R-trans-E |
| 19 | Pr | H | 1R-trans-E |
| 20 | Pr | Me | 1R-trans-E |
| 21 | i-Pr | H | 1R-trans-E |
| 22 | i-Pr | Me | 1R-trans-E |
| 23 | CF$_3$CH$_2$ | Me | 1R-trans-E |
| 24 | allyl | Me | 1R-trans-E |
| 25 | propargyl | Me | 1R-trans-E |

TABLE 2

| Compound No. | R | X | Configuration of acid component |
|---|---|---|---|
| 26 | H | H | 1R-trans-Z |
| 27 | H | F | 1R-trans-Z |
| 28 | H | Me | 1R-trans-Z |
| 29 | H | allyl | 1R-trans-Z |
| 30 | H | propargyl | 1R-trans-Z |
| 31 | H | MeOCH$_2$ | 1R-trans-Z |
| 32 | H | MeO | 1R-trans-Z |
| 33 | H | MeS | 1R-trans-Z |
| 34 | Me | H | 1R-trans-Z |
| 35 | Me | F | 1R-trans-Z |
| 36 | Me | Me | 1R-trans-Z |
| 37 | Me | allyl | 1R-trans-Z |
| 38 | Me | propargyl | 1R-trans-Z |
| 39 | Me | MeOCH$_2$ | 1R-trans-Z |
| 40 | Me | MeO | 1R-trans-Z |
| 41 | Me | MeS | 1R-trans-Z |
| 42 | Et | H | 1R-trans-Z |
| 43 | Et | Me | 1R-trans-Z |
| 44 | Pr | H | 1R-trans-Z |
| 45 | Pr | Me | 1R-trans-Z |
| 46 | i-Pr | H | 1R-trans-Z |
| 47 | i-Pr | Me | 1R-trans-Z |
| 48 | CF$_3$CH$_2$ | Me | 1R-trans-Z |
| 49 | allyl | Me | 1R-trans-Z |
| 50 | propargyl | Me | 1R-trans-Z |

TABLE 3

| Compound No. | R | X | Configuration of acid component |
|---|---|---|---|
| 51 | H | H | 1R-cis-E |
| 52 | H | F | 1R-cis-E |
| 53 | H | Me | 1R-cis-E |
| 54 | H | allyl | 1R-cis-E |
| 55 | H | propargyl | 1R-cis-E |
| 56 | H | MeOCH$_2$ | 1R-cis-E |
| 57 | H | MeO | 1R-cis-E |
| 58 | H | MeS | 1R-cis-E |
| 59 | Me | H | 1R-cis-E |
| 60 | Me | F | 1R-cis-E |
| 61 | Me | Me | 1R-cis-E |
| 62 | Me | allyl | 1R-cis-E |
| 63 | Me | propargyl | 1R-cis-E |
| 64 | Me | MeOCH$_2$ | 1R-cis-E |
| 65 | Me | MeO | 1R-cis-E |
| 66 | Me | MeS | 1R-cis-E |
| 67 | Et | H | 1R-cis-E |
| 68 | Et | Me | 1R-cis-E |
| 69 | Pr | H | 1R-cis-E |
| 70 | Pr | Me | 1R-cis-E |
| 71 | i-Pr | H | 1R-cis-E |
| 72 | i-Pr | Me | 1R-cis-E |
| 73 | CF$_3$CH$_2$ | Me | 1R-cis-E |
| 74 | allyl | Me | 1R-cis-E |
| 75 | propargyl | Me | 1R-cis-E |

TABLE 4

| Compound No. | R | X | Configuration of acid component |
|---|---|---|---|
| 76 | H | H | 1R-cis-Z |
| 77 | H | F | 1R-cis-Z |
| 78 | H | Me | 1R-cis-Z |
| 79 | H | allyl | 1R-cis-Z |
| 80 | H | propargyl | 1R-cis-Z |
| 81 | H | MeOCH$_2$ | 1R-cis-Z |
| 82 | H | MeO | 1R-cis-Z |
| 83 | H | MeS | 1R-cis-Z |
| 84 | Me | H | 1R-cis-Z |
| 85 | Me | F | 1R-cis-Z |
| 86 | Me | Me | 1R-cis-Z |
| 87 | Me | allyl | 1R-cis-Z |
| 88 | Me | propargyl | 1R-cis-Z |

TABLE 4-continued

| Compound No. | R | X | Configuration of acid component |
|---|---|---|---|
| 89 | Me | MeOCH$_2$ | 1R-cis-Z |
| 90 | Me | MeO | 1R-cis-Z |
| 91 | Me | MeS | 1R-cis-Z |
| 92 | Et | H | 1R-cis-Z |
| 93 | Et | Me | 1R-cis-Z |
| 94 | Pr | H | 1R-cis-Z |
| 95 | Pr | Me | 1R-cis-Z |
| 96 | i-Pr | H | 1R-cis-Z |
| 97 | i-Pr | Me | 1R-cis-Z |
| 98 | CF$_3$CH$_2$ | Me | 1R-cis-Z |
| 99 | allyl | Me | 1R-cis-Z |
| 100 | propargyl | Me | 1R-cis-Z |

TABLE 5

| Compound No. | R | X | Configuration of acid component |
|---|---|---|---|
| 101 | H | H | 1RS-trans-E |
| 102 | H | F | 1RS-trans-E |
| 103 | H | Me | 1RS-trans-E |
| 104 | H | allyl | 1RS-trans-E |
| 105 | H | propargyl | 1RS-trans-E |
| 106 | H | MeOCH$_2$ | 1RS-trans-E |
| 107 | H | MeO | 1RS-trans-E |
| 108 | H | MeS | 1RS-trans-E |
| 109 | Me | H | 1RS-trans-E |
| 110 | Me | F | 1RS-trans-E |
| 111 | Me | Me | 1RS-trans-E |
| 112 | Me | allyl | 1RS-trans-E |
| 113 | Me | propargyl | 1RS-trans-E |
| 114 | Me | MeOCH$_2$ | 1RS-trans-E |
| 115 | Me | MeO | 1RS-trans-E |
| 116 | Me | MeS | 1RS-trans-E |
| 117 | Et | H | 1RS-trans-E |
| 118 | Et | Me | 1RS-trans-E |
| 119 | Pr | H | 1RS-trans-E |
| 120 | Pr | Me | 1RS-trans-E |
| 121 | i-Pr | H | 1RS-trans-E |
| 122 | i-Pr | Me | 1RS-trans-E |
| 123 | CF$_3$CH$_2$ | Me | 1RS-trans-E |
| 124 | allyl | Me | 1RS-trans-E |
| 125 | propargyl | Me | 1RS-trans-E |

TABLE 6

| Compound No. | R | X | Configuration of acid component |
|---|---|---|---|
| 126 | H | H | 1RS-trans-Z |
| 127 | H | F | 1RS-trans-Z |
| 128 | H | Me | 1RS-trans-Z |
| 129 | H | allyl | 1RS-trans-Z |
| 130 | H | propargyl | 1RS-trans-Z |
| 131 | H | MeOCH$_2$ | 1RS-trans-Z |
| 132 | H | MeO | 1RS-trans-Z |
| 133 | H | MeS | 1RS-trans-Z |
| 134 | Me | H | 1RS-trans-Z |
| 135 | Me | F | 1RS-trans-Z |
| 136 | Me | Me | 1RS-trans-Z |
| 137 | Me | allyl | 1RS-trans-Z |
| 138 | Me | propargyl | 1RS-trans-Z |
| 139 | Me | MeOCH$_2$ | 1RS-trans-Z |
| 140 | Me | MeO | 1RS-trans-Z |
| 141 | Me | MeS | 1RS-trans-Z |
| 142 | Et | H | 1RS-trans-Z |
| 143 | Et | Me | 1RS-trans-Z |
| 144 | Pr | H | 1RS-trans-Z |
| 145 | Pr | Me | 1RS-trans-Z |
| 146 | i-Pr | H | 1RS-trans-Z |
| 147 | i-Pr | Me | 1RS-trans-Z |

TABLE 6-continued

| Compound No. | R | X | Configuration of acid component |
|---|---|---|---|
| 148 | CF$_3$CH$_2$ | Me | 1RS-trans-Z |
| 149 | allyl | Me | 1RS-trans-Z |
| 150 | propargyl | Me | 1RS-trans-Z |

TABLE 7

| Compound No. | R | X | Configuration of acid component |
|---|---|---|---|
| 151 | H | H | 1RS-cis-E |
| 152 | H | F | 1RS-cis-E |
| 152 | H | Me | 1RS-cis-E |
| 154 | H | allyl | 1RS-cis-E |
| 155 | H | propargyl | 1RS-cis-E |
| 156 | H | MeOCH$_2$ | 1RS-cis-E |
| 157 | H | MeO | 1RS-cis-E |
| 158 | H | MeS | 1RS-cis-E |
| 159 | Me | H | 1RS-cis-E |
| 160 | Me | F | 1RS-cis-E |
| 161 | Me | Me | 1RS-cis-E |
| 162 | Me | allyl | 1RS-cis-E |
| 163 | Me | propargyl | 1RS-cis-E |
| 164 | Me | MeOCH$_2$ | 1RS-cis-E |
| 165 | Me | MeO | 1RS-cis-E |
| 166 | Me | MeS | 1RS-cis-E |
| 167 | Et | H | 1RS-cis-E |
| 168 | Et | Me | 1RS-cis-E |
| 169 | Pr | H | 1RS-cis-E |
| 170 | Pr | Me | 1RS-cis-E |
| 171 | i-Pr | H | 1RS-cis-E |
| 172 | i-Pr | Me | 1RS-cis-E |
| 173 | CF$_3$CH$_2$ | Me | 1RS-cis-E |
| 174 | allyl | Me | 1RS-cis-E |
| 175 | propargyl | Me | 1RS-cis-E |

TABLE 8

| Compound No. | R | X | Configuration of acid component |
|---|---|---|---|
| 176 | H | H | 1RS-cis-Z |
| 177 | H | F | 1RS-cis-Z |
| 178 | H | Me | 1RS-cis-Z |
| 179 | H | allyl | 1RS-cis-Z |
| 180 | H | propargyl | 1RS-cis-Z |
| 181 | H | MeOCH$_2$ | 1RS-cis-Z |
| 182 | H | MeO | 1RS-cis-Z |
| 183 | H | MeS | 1RS-cis-Z |
| 184 | Me | H | 1RS-cis-Z |
| 185 | Me | F | 1RS-cis-Z |
| 186 | Me | Me | 1RS-cis-Z |
| 187 | Me | allyl | 1RS-cis-Z |
| 188 | Me | propargyl | 1RS-cis-Z |
| 189 | Me | MeOCH$_2$ | 1RS-cis-Z |
| 190 | Me | MeO | 1RS-cis-Z |
| 191 | Me | MeS | 1RS-cis-Z |
| 192 | Et | H | 1RS-cis-Z |
| 193 | Et | Me | 1RS-cis-Z |
| 194 | Pr | H | 1RS-cis-Z |
| 195 | Pr | Me | 1RS-cis-Z |
| 196 | i-Pr | H | 1RS-cis-Z |
| 197 | i-Pr | Me | 1RS-cis-Z |
| 198 | CF$_3$CH$_2$ | Me | 1RS-cis-Z |
| 199 | allyl | Me | 1RS-cis-Z |
| 200 | propargyl | Me | 1RS-cis-Z |

TABLE 9

| Compound No. | R | X | Configuration of acid component |
| --- | --- | --- | --- |
| 201 | Et | MeO | 1R-trans-E |
| 202 | Et | allyl | 1R-trans-E |
| 203 | Et | Propargyl | 1R-trans-E |
| 204 | Et | MeOCH$_2$ | 1R-trans-E |
| 205 | Pr | MeO | 1R-trans-E |
| 206 | Pr | allyl | 1R-trans-E |
| 207 | Pr | Propargyl | 1R-trans-E |
| 208 | Pr | MeOCH$_2$ | 1R-trans-E |
| 209 | i-Pr | MeO | 1R-trans-E |
| 210 | i-Pr | allyl | 1R-trans-E |
| 211 | i-Pr | Propargyl | 1R-trans-E |
| 212 | i-Pr | MeOCH$_2$ | 1R-trans-E |
| 213 | CF$_3$CH$_2$ | H | 1R-trans-E |
| 214 | CF$_3$CH$_2$ | MeO | 1R-trans-E |
| 215 | CF$_3$CH$_2$ | allyl | 1R-trans-E |
| 216 | CF$_3$CH$_2$ | Propargyl | 1R-trans-E |
| 217 | CF$_3$CH$_2$ | MeOCH$_2$ | 1R-trans-E |
| 218 | allyl | H | 1R-trans-E |
| 219 | allyl | MeO | 1R-trans-E |
| 220 | H | Cl | 1R-trans-E |
| 221 | Me | Cl | 1R-trans-E |
| 222 | Et | Cl | 1R-trans-E |
| 223 | H | CF$_3$ | 1R-trans-E |
| 224 | Me | CF$_3$ | 1R-trans-E |
| 225 | Et | CF$_3$ | 1R-trans-E |

TABLE 10

| Compound No. | R | X | Configuration of acid component |
| --- | --- | --- | --- |
| 226 | Et | MeO | 1R-trans-Z |
| 227 | Et | allyl | 1R-trans-Z |
| 228 | Et | Propargyl | 1R-trans-Z |
| 229 | Et | MeOCH$_2$ | 1R-trans-Z |
| 230 | Pr | MeO | 1R-trans-Z |
| 231 | Pr | allyl | 1R-trans-Z |
| 232 | Pr | Propargyl | 1R-trans-Z |
| 233 | Pr | MeOCH$_2$ | 1R-trans-Z |
| 234 | i-Pr | MeO | 1R-trans-Z |
| 235 | i-Pr | allyl | 1R-trans-Z |
| 236 | i-Pr | Propargyl | 1R-trans-Z |
| 237 | i-Pr | MeOCH$_2$ | 1R-trans-Z |
| 238 | CF$_3$CH$_2$ | H | 1R-trans-Z |
| 239 | CF$_3$CH$_2$ | MeO | 1R-trans-Z |
| 240 | CF$_3$CH$_2$ | allyl | 1R-trans-Z |
| 241 | CF$_3$CH$_2$ | Propargyl | 1R-trans-Z |
| 242 | CF$_3$CH$_2$ | MeOCH$_2$ | 1R-trans-Z |
| 243 | allyl | H | 1R-trans-Z |
| 244 | allyl | MeO | 1R-trans-Z |
| 245 | H | Cl | 1R-trans-Z |
| 246 | Me | Cl | 1R-trans-Z |
| 247 | Et | Cl | 1R-trans-Z |
| 248 | H | CF$_3$ | 1R-trans-Z |
| 249 | Me | CF$_3$ | 1R-trans-Z |
| 250 | Et | CF$_3$ | 1R-trans-Z |

TABLE 11

| Compound No. | R | X | Configuration of acid component |
| --- | --- | --- | --- |
| 251 | Et | MeO | 1R-cis-E |
| 252 | Et | allyl | 1R-cis-E |
| 253 | Et | Propargyl | 1R-cis-E |
| 254 | Et | MeOCH$_2$ | 1R-cis-E |
| 255 | Pr | MeO | 1R-cis-E |
| 256 | Pr | allyl | 1R-cis-E |
| 257 | Pr | Propargyl | 1R-cis-E |
| 258 | Pr | MeOCH$_2$ | 1R-cis-E |
| 259 | i-Pr | MeO | 1R-cis-E |
| 260 | i-Pr | allyl | 1R-cis-E |
| 261 | i-Pr | Propargyl | 1R-cis-E |
| 262 | i-Pr | MeOCH$_2$ | 1R-cis-E |
| 263 | CF$_3$CH$_2$ | H | 1R-cis-E |
| 264 | CF$_3$CH$_2$ | MeO | 1R-cis-E |
| 265 | CF$_3$CH$_2$ | allyl | 1R-cis-E |
| 266 | CF$_3$CH$_2$ | Propargyl | 1R-cis-E |
| 267 | CF$_3$CH$_2$ | MeOCH$_2$ | 1R-cis-E |
| 268 | allyl | H | 1R-cis-E |
| 269 | allyl | MeO | 1R-cis-E |
| 270 | H | Cl | 1R-cis-E |
| 271 | Me | Cl | 1R-cis-E |
| 272 | Et | Cl | 1R-cis-E |
| 273 | H | CF$_3$ | 1R-cis-E |
| 274 | Me | CF$_3$ | 1R-cis-E |
| 275 | Et | CF$_3$ | 1R-cis-E |

TABLE 12

| Compound No. | R | X | Configuration of acid component |
| --- | --- | --- | --- |
| 276 | Et | MeO | 1R-cis-Z |
| 277 | Et | allyl | 1R-cis-Z |
| 278 | Et | Propargyl | 1R-cis-Z |
| 279 | Et | MeOCH$_2$ | 1R-cis-Z |
| 280 | Pr | MeO | 1R-cis-Z |
| 281 | Pr | allyl | 1R-cis-Z |
| 282 | Pr | Propargyl | 1R-cis-Z |
| 283 | Pr | MeOCH$_2$ | 1R-cis-Z |
| 284 | i-Pr | MeO | 1R-cis-Z |
| 285 | i-Pr | allyl | 1R-cis-Z |
| 286 | i-Pr | Propargyl | 1R-cis-Z |
| 287 | i-Pr | MeOCH$_2$ | 1R-cis-Z |
| 288 | CF$_3$CH$_2$ | H | 1R-cis-Z |
| 289 | CF$_3$CH$_2$ | MeO | 1R-cis-Z |
| 290 | CF$_3$CH$_2$ | allyl | 1R-cis-Z |
| 291 | CF$_3$CH$_2$ | Propargyl | 1R-cis-Z |
| 292 | CF$_3$CH$_2$ | MeOCH$_2$ | 1R-cis-Z |
| 293 | allyl | H | 1R-cis-Z |
| 294 | allyl | MeO | 1R-cis-Z |
| 295 | H | Cl | 1R-cis-Z |
| 296 | Me | Cl | 1R-cis-Z |
| 297 | Et | Cl | 1R-cis-Z |
| 298 | H | CF$_3$ | 1R-cis-Z |
| 299 | Me | CF$_3$ | 1R-cis-Z |
| 300 | Et | CF$_3$ | 1R-cis-Z |

TABLE 13

| Compound No. | R | X | Configuration of acid component |
| --- | --- | --- | --- |
| 301 | Et | MeO | 1RS-trans-E |
| 302 | Et | allyl | 1RS-trans-E |
| 303 | Et | Propargyl | 1RS-trans-E |
| 304 | Et | MeOCH$_2$ | 1RS-trans-E |
| 305 | Pr | MeO | 1RS-trans-E |
| 306 | Pr | allyl | 1RS-trans-E |
| 307 | Pr | Propargyl | 1RS-trans-E |
| 308 | Pr | MeOCH$_2$ | 1RS-trans-E |
| 309 | i-Pr | MeO | 1RS-trans-E |
| 310 | i-Pr | allyl | 1RS-trans-E |
| 311 | i-Pr | Propargyl | 1RS-trans-E |
| 312 | i-Pr | MeOCH$_2$ | 1RS-trans-E |
| 313 | CF$_3$CH$_2$ | H | 1RS-trans-E |
| 314 | CF$_3$CH$_2$ | MeO | 1RS-trans-E |
| 315 | CF$_3$CH$_2$ | allyl | 1RS-trans-E |
| 316 | CF$_3$CH$_2$ | Propargyl | 1RS-trans-E |
| 317 | CF$_3$CH$_2$ | MeOCH$_2$ | 1RS-trans-E |
| 318 | allyl | H | 1RS-trans-E |

TABLE 13-continued

| Compound No. | R | X | Configuration of acid component |
| --- | --- | --- | --- |
| 319 | allyl | MeO | 1RS-trans-E |
| 320 | H | Cl | 1RS-trans-E |
| 321 | Me | Cl | 1RS-trans-E |
| 322 | Et | Cl | 1RS-trans-E |
| 323 | H | $CF_3$ | 1RS-trans-E |
| 324 | Me | $CF_3$ | 1RS-trans-E |
| 325 | Et | $CF_3$ | 1RS-trans-E |

TABLE 14

| Compound No. | R | X | Configuration of acid component |
| --- | --- | --- | --- |
| 326 | E t | MeO | 1RS-trans-Z |
| 327 | E t | allyl | 1RS-trans-Z |
| 328 | E t | Propargyl | 1RS-trans-Z |
| 329 | E t | $MeOCH_2$ | 1RS-trans-Z |
| 330 | Pr | MeO | 1RS-trans-Z |
| 331 | Pr | allyl | 1RS-trans-Z |
| 332 | Pr | Propargyl | 1RS-trans-Z |
| 333 | Pr | $MeOCH_2$ | 1RS-trans-Z |
| 334 | i-Pr | MeO | 1RS-trans-Z |
| 335 | i-Pr | allyl | 1RS-trans-Z |
| 336 | i-Pr | Propargyl | IRS-trans-Z |
| 337 | i-Pr | $MeOCH_2$ | 1RS-trans-Z |
| 338 | $CF_3CH_2$ | H | 1RS-trans-Z |
| 339 | $CF_3CH_2$ | MeO | 1RS-trans-Z |
| 340 | $CF_3CH_2$ | allyl | 1RS-trans-Z |
| 341 | $CF_3CH_2$ | Propargyl | 1RS-trans-Z |
| 342 | $CF_3CH_2$ | $MeOCH_2$ | 1RS-trans-Z |
| 343 | allyl | H | 1RS-trans-Z |
| 344 | allyl | MeO | 1RS-trans-Z |
| 345 | H | Cl | 1RS-trans-Z |
| 346 | Me | Cl | 1RS-trans-Z |
| 347 | Et | Cl | 1RS-trans-Z |
| 348 | H | $CF_3$ | 1RS-trans-Z |
| 349 | Me | $CF_3$ | 1RS-trans-Z |
| 350 | Et | $CF_3$ | 1RS-trans-Z |

TABLE 15

| Compound No. | R | X | Configuration of acid component |
| --- | --- | --- | --- |
| 351 | E t | MeO | 1RS-cis-E |
| 352 | E t | allyl | 1RS-cis-E |
| 353 | E t | Propargyl | 1RS-cis-E |
| 354 | E t | $MeOCH_2$ | 1RS-cis-E |
| 355 | Pr | MeO | 1RS-cis-E |
| 356 | Pr | allyl | 1RS-cis-E |
| 357 | Pr | Propargyl | 1RS-cis-E |
| 358 | Pr | $MeOCH_2$ | 1RS-cis-E |
| 359 | i-Pr | MeO | 1RS-cis-E |
| 360 | i-Pr | allyl | 1RS-cis-E |
| 361 | i-Pr | Propargyl | 1RS-cis-E |
| 362 | i-Pr | $MeOCH_2$ | 1RS-cis-E |
| 363 | $CF_3CH_2$ | H | 1RS-cis-E |
| 364 | $CF_3CH_2$ | MeO | 1RS-cis-E |
| 365 | $CF_3CH_2$ | allyl | 1RS-cis-E |
| 366 | $CF_3CH_2$ | Propargyl | 1RS-cis-E |
| 367 | $CF_3CH_2$ | $MeOCH_2$ | 1RS-cis-E |
| 368 | allyl | H | 1RS-cis-E |
| 369 | allyl | MeO | 1RS-cis-E |
| 370 | H | Cl | 1RS-cis-E |
| 371 | Me | Cl | 1RS-cis-E |
| 372 | Et | Cl | 1RS-cis-E |
| 373 | H | $CF_3$ | 1RS-cis-E |
| 374 | Me | $CF_3$ | 1RS-cis-E |
| 375 | Et | $CF_3$ | 1RS-cis-E |

TABLE 16

| Compound No. | R | X | Configuration of acid component |
| --- | --- | --- | --- |
| 376 | E t | MeO | 1RS-cis-Z |
| 377 | E t | allyl | 1RS-cis-Z |
| 378 | E t | Propargyl | 1RS-cis-Z |
| 379 | E t | $MeOCH_2$ | 1RS-cis-Z |
| 380 | Pr | MeO | 1RS-cis-Z |
| 381 | Pr | allyl | 1RS-cis-Z |
| 382 | Pr | Propargyl | 1RS-cis-Z |
| 383 | Pr | $MeOCH_2$ | 1RS-cis-Z |
| 384 | i-Pr | MeO | 1RS-cis-Z |
| 385 | i-Pr | allyl | 1RS-cis-Z |
| 386 | i-Pr | Propargyl | 1RS-cis-Z |
| 387 | i-Pr | $MeOCH_2$ | 1RS-cis-Z |
| 388 | $CF_3CH_2$ | H | 1RS-cis-Z |
| 389 | $CF_3CH_2$ | MeO | 1RS-cis-Z |
| 390 | $CF_3CH_2$ | allyl | 1RS-cis-Z |
| 391 | $CF_3CH_2$ | Propargyl | 1RS-cis-Z |
| 392 | $CF_3CH_2$ | $MeOCH_2$ | 1RS-cis-Z |
| 393 | allyl | H | 1RS-cis-Z |
| 394 | allyl | MeO | 1RS-cis-Z |
| 395 | H | Cl | 1RS-cis-Z |
| 396 | Me | Cl | 1RS-cis-Z |
| 397 | Et | Cl | 1RS-cis-Z |
| 398 | H | $CF_3$ | 1RS-cis-Z |
| 399 | Me | $CF_3$ | 1RS-cis-Z |
| 400 | Et | $CF_3$ | 1RS-cis-Z |

Next, the physical property values of the present compounds are described below.

Present Compound 9
$^1$H-NMR (CDCl$_3$, TMS) δ 1.21 (3H, s), 1.29 (3H, s), 1.88 (1H, d, J=5.4), 2.21 (1H, dd, J=7.2, 5.4), 3.83 (3H, s), 5.24 (2H, br s), 7.10 (1H, tt, J=9.7, 7.4), 7.19 (1H, d, J=7.2).

Present Compound 10
$^1$H-NMR (CDCl$_3$, TMS) δ 1.21 (3H, s), 1.29 (3H, s), 1.87 (1H, d, J=5.4), 2.21 (1H, dd, J=7.5, 5.4), 3.83 (3H, s), 5.21 (2H, s), 7.19 (1H, d, J=7.5).

Present Compound 11
$^1$H-NMR (CDCl$_3$, TMS) δ 1.20 (3H, s), 1.29 (3H, s), 1.87 (1H, d, J=5.5), 2.21 (1H, dd, J=7.5, 5.5), 2.29 (3H, t, J=2.1), 3.83 (3H, s), 5.21 (2H, br s), 7.18 (1H, d, J=7.5).

Present Compound 15
$^1$H-NMR (CDCl$_3$, TMS) δ 1.20 (3H, s), 1.29 (3H, s), 1.86 (1H, d, J=5.5), 2.21 (1H, dd, J=7.4, 5.5), 3.83 (3H, s), 4.10 (3H, t, J=1.5), 5.18 (1H, t, J=1.4), 5.19 (1H, t, J=1.4), 7.19 (1H, d, J=7.4).

Present Compound 34
$^1$H-NMR (CDCl$_3$, TMS) δ 1.23 (3H, s), 1.30 (3H, s), 1.76 (1H, d, J=5.5), 2.70 (1H, dd, J=7.8, 5.5), 3.89 (3H, s), 5.25 (2H, br s), 6.31 (1H, d, J=7.8), 7.10 (1H, tt, J=9.7, 7.4).

Present Compound 35
$^1$H-NMR (CDCl$_3$, TMS) δ 1.23 (3H, s), 1.29 (3H, s), 1.74 (1H, d, J=5.5), 2.69 (1H, dd, J=7.9, 5.5), 3.89 (3H, s), 5.22 (2H, br s), 6.31 (1H, d, J=7.9).

Present Compound 36
$^1$H-NMR (CDCl$_3$, TMS) δ 1.23 (3H, s), 1.30 (3H, s), 1.76 (1H, d, J=5.6), 2.29 (2H, t, J=2.1), 2.69 (1H, dd, J=7.8, 5.6), 3.89 (3H, s), 5.23 (2H, br s), 6.31 (1H, d, J=7.8).

Present Compound 40
$^1$H-NMR (CDCl$_3$, TMS) δ 1.23 (3H, s), 1.30 (3H, s), 1.75 (1H, d, J=5.5), 2.70 (1H, dd, J=7.9, 5.5), 3.89 (3H, s), 4.10 (3H, t, J=1.5), 5.19 (1H, t, J=1.5), 5.20 (1H, t, J=1.5), 6.31 (1H, d, J=7.9).

1:1 Mixture of Present Compound 61 and Present Compound 86
$^1$H-NMR (CDCl$_3$, TMS) δ 1.23 (1.5H, s), 1.24 (1.5H, s), 1.32 (3H, s), 1.85 (0.5H, s), 1.88 (0.5H, s), 2.00 (0.5H, t, J=8.7), 2.29 (3H, t, J=2.1), 2.47 (0.5H, dd, J=8.7, 7.9), 3.84

(1.5H, s), 3.89 (1.5H, s), 5.20 (2H, br s), 6.99 (0.5H, d, J=7.9), 7.69 (0.5H, d, J=8.7).

Present Compound 3

$^1$H-NMR (CDCl$_3$, TMS) δ 1.21 (3H, s, 1.30 (3H, s), 1.87 (1H, d, J=5.5), 2.21 (1H, dd, J=7.1, 5.5), 2.29 (3H, t, J=2.1), 5.22 (2H, s), 6.99 (1H, s), 7.26 (1H, d, J=7.1).

Present Compound 20

$^1$H-NMR (CDCl$_3$, TMS) δ 0.92 (3H, t, J=7.6), 1.20 (3H, s), 1.29 (3H, s), 1.65 (2H, qt, J=7.6, 6.8), 1.86 (1H, d, J=5.5), 2.21 (1H, dd, J=7.4, 5.5), 2.29 (3H, t, J=2.0), 3.97 (2H, t, J=6.9), 5.21 (2H, br s), 7.20 (1H, d, J=7.4)

Present Compound 24

$^1$H-NMR (CDCl$_3$, TMS) δ 1.20 (3H, s), 1.29 (3H, s), 1.87 (1H, d, J=5.4), 2.20 (1H, dd, J=7.3, 5.4), 2.29 (3H, t, J=2.1), 4.53 (2H, dt, J=5.8, 1.4), 5.21 (2H, br s), 5.22 (1H, dd, J=10.4, 1.6), 5.29 (1H, dd, J=17.1, 1.6), 5.97 (1H, ddt, J=17.1, 10.4, 5.8) 7.24 (1H, d, J=7.3).

Present Compound 28

$^1$H-NMR (CDCl$_3$, TMS) δ 1.24 (3H, s), 1.32 (3H, s), 1.77 (1H, d, J=5.7), 2.29 (3H, t, J=2.2), 2.76 (1H, dd, J=7.7, 5.7), 5.23 (2H, s), 6.41 (1H, d, J=7.7), 7.33 (1H, s).

Present Compound 49

$^1$H-NMR (CDCl$_3$, TMS) δ 1.22 (3H, s), 1.30 (3H, s), 1.75 (1H, d, J=5.5), 2.29 (3H, t, J=2.1), 2.73 (1H, dd, J=7.8, 5.5), 4.59 (2H, br d, J=5.7), 5.21 (1H, dd, J=10.4, 1.5), 5.23 (2H, br s), 5.29 (1H, dd, J=17.3, 1.5), 5.99 (1H, ddt, J=17.3, 10.4, 5.7), 6.35 (1H, d, J=7.8).

1:1 Mixture of Present Compound 14 and Present Compound 39

$^1$H-NMR (CDCl$_3$, TMS) δ 1.21 (1.5H), 1.23 (1.5H), 1.29 (1.5H, s), 1.30 (1.5H, s), 1.75 (0.5H, d, J=5.4), 1.87 (0.5H, s), 2.21 (0.5H, dd, J=7.2, 5.6), 2.69 (0.5H, dd, J=7.6, 5.4), 3.41 (3H, s), 3.82 (1.5H, s), 3.89 (1.5H, s), 4.59 (2H, s), 5.24 (2H, s), 6.31 (0.5H, d, J=7.8), 7.19 (0.5H, d, J=7.2).

1:1 Mixture of Present Compound 23 and Present Compound 48

$^1$H-NMR (CDCl$_3$, TMS) δ 1.20 (1.5H, s), 1.22 (1.5H, s), 1.30 (3H, s), 1.78 (0.5H, d, J=5.6), 1.92 (0.5H, d, J=5.4), 2.19 (0.5H, dd, J=7.1, 5.4), 2.29 (3H, t, J=2.1), 2.66 (0.5H, dd, J=7.5, 5.6), 4.32–4.48 (2H, M), 5.23 (2H, br s), 6.42 (0.5H, d, J=7.5), 7.34 (0.5H, d, J=7.1).

1:1 Mixture of Present Compound 59 and Present Compound 84

$^1$H-NMR (CDCl$_3$, TMS) δ 1.24 (1.5H, s), 1.25 (1.5H, s), 1.32 (3H, s), 1.86 (0.5H, d, J=8.5), 1.89 (0.5H, d, J=8.7), 2.01 (0.5H, dd, J=9.0, 8.5), 2.48 (0.5H, dd, J=8.7, 7.7), 3.84 (1.5H, s), 3.89 (1.5H, s), 5.23 (2H, br s), 6.99 (0.5H, d, J=7.7), 7.10 (1H, tt, J=9.6, 7.4), 7.68 (0.5H, d, J=9.0).

1:1 Mixture of Present Compound 65 and Present Compound 90

$^1$H-NMR (CDCl$_3$, TMS) δ 1.23 (1.5H, s), 1.25 (1.5H, s), 1.32 (3H, s), 1.84 (0.5H, d, J=8.6), 1.88 (0.5H, d, J=8.6), 2.00 (0.5H, dd, J=8.9, 8.6), 2.48 (0.5, dd, J=8.6, 7.9), 3.84 (1.5H, s), 3.89 (1.5H, s), 4.10 (3H, t, J=1.5), 5.17 (2H, t, J=1.4), 7.00 (0.5H, d, J=7.9), 7.68 (0.5H, d, J=8.9).

3:2 Mixture of Present Compound 214 and Present Compound 239

$^1$H-NMR (CDCl$_3$, TMS) δ 1.21 (1.8H, s), 1.23 (1.2H), 1.30 (3H, s), 1.78 (0.4H, d, J=5.5), 1.92 (0.6H, d, J=5.5), 2.20 (0.6H, dd, J=7.2, 5.5), 2.67 (0.4H, dd, J=7.5, 5.5), 4.08 (1.2H, t, J=1.5), 4.10 (1.8H, t, J=1.5), 4.32–4.48 (2H, M), 5.18–5.22 (2H, M), 6.42 (0.4H, d, J=7.6), 7.34 (0.6H, d, J=7.2).

3:2 Mixture of Present Compound 219 and Present Compound 244

$^1$H-NMR (CDCl$_3$, TMS) δ 1.20 (1.8H, s), 1.23 (1.2H), 1.29 (1.8H, s), 1.31 (1.2H, s), 1.75 (0.4H, d, J=5.5), 1.87 (0.6H, d, J=5.5), 2.23 (0.6H, dd, J=7.5, 5.5), 2.73 (0.4H, dd, J=7.8, 5.5), 4.10 (3H, t, J=1.5), 4.52 (1.2H, dt, J=5.8, 1.3), 4.59 (0.8H, dt, J=5.6, 1.4), 5.18–5.33 (4H, M), 5.89–6.07 (1H, M), 6.35 (0.4H, d, J=7.8), 7.24 (0.6H, d, J=7.5).

Next, formulation examples are described below. In the formulation examples, parts are all by weight, and the present compounds are identified by the compound number shown in Tables 1 to 8.

Formulation Example 1

Emulsifiable Concentrates

10% Emulsifiable concentrates of each of the present compounds 1 to 200 are obtained by dissolving 10 parts of each of the present compounds in a mixture of 35 parts of xylene and 35 parts of dimethylformamide, adding thereto 14 parts of polyoxyethylene styryl phenyl ether and 6 parts of calcium dodecylbenzenesulfonate, and thoroughly stirring and mixing the resultant mixture.

Formulation Example 2

Wettable Powders

20% Wettable powders of each of the present compounds 1 to 200 are obtained by adding 20 parts of each of the present compounds to a mixture of 4 parts of sodium lauryl sulfate, 2 parts of calcium lignosulfonate, 20 parts of fine powder of synthetic hydrated silicon dioxide and 54 parts of diatomaceous earth, and stirring and mixing the resultant mixture in a juice mixer.

Formulation Example 3

Granules

5 Parts of fine powder of synthetic hydrated silicon dioxide, 5 parts of sodium dodecylbenzenesulfonate, 30 parts of bentonite and 55 parts of clay were added to 5 parts of each, of the present compounds 1 to 200. The resultant mixture was thoroughly stirred and mixed. Thereafter, an appropriate quantity of water was added to the resulting mixture and further stirred. The thus stirred mixture was subjected to particle size regulation with a granulator and then through-flow drying, to obtain 5% granules of each of the present compounds.

Formulation Example 4

Dusts

1% Dusts of each of the present compounds 1 to 200 are obtained by dissolving 1 part of each of the present compounds in an appropriate quantity of acetone, adding thereto 5 parts of fire powder of synthetic hydrated silicon dioxide, 0.3 part of PAP and 93.7 parts of clay, mixing them in a juice mixer, and then removing the acetone by evaporation.

Formulation Example 5

Flowable Concentrates

20% Flowable concentrates of each of the present compounds 1 to 200 are obtained by mixing 20 parts of each of the present compounds, 1.5 parts of sorbitan trioleate and 28.5 parts of an aqueous solution containing 2 parts of a poly(vinyl alcohol), finely grinding the resulting mixtures to a particle size of 3 μm or less with a sand grinder, and adding thereto 40 parts of an aqueous solution which contains 0.05 part of xanthan gum and 0.1 part of aluminum magnesium silicate, as well as 10 parts of propylene glycol, and stirring and mixing the resultant mixture.

Formulation Example 6
Oil Formulations 0.1% Oil formulations of each of the present compounds 1 to 200 are obtained by dissolving 0.1 part of each of the present compounds in 10 parts of dichloromethane and mixing the resulting solution with 89.9 parts of deodorized kerosene.

Formulation Example 7
Oil-based Aerosols

Oil-based aerosols of each of the present compounds 1 to 200 are obtained by mixing 1 part of each of the present compounds, 5 parts of dichloromethane and 34 parts of deodorized kerosene to obtain a solution, charging the resulting solution into an aerosol container, attaching a valve part to the container, and then compressing 60 parts of a propellant (liquefied petroleum gas) into the container under pressure through the valve part.

Formulation Example 8
Water-based Aerosols

Water-based aerosols of each of the present compounds 1 to 200 are obtained by mixing 0.6 part of each of the present compounds, 5 parts of xylene, 3.4 parts of deodorized kerosene and 1 part of an emulsifier {Atmos 300 (a registered trade name, Atlas Chemical Corp.)} to obtain a solution, charging the resulting solution with 50 parts of pure water into an aerosol container, attaching a valve part to the container, and then compressing 40 parts of a propellant (liquefied petroleum gas) into the container under pressure through the valve part.

Formulation Example 9
Mosquito Coils

Mosquito coils for controlling insects and/or acarines are obtained by impregnating a base material for mosquito coil (a material prepared by uniformly stirring and mixing Tabu powder, Pyrethrum marc and wood powder in a ratio of 4:3:3 to obtain a carrier for mosquito coil, adding 120 ml of water to 99.5 g of the carrier for mosquito coil, thoroughly kneading the resulting mixture, and molding and drying the kneaded mixture) with an acetone solution containing 0.5 g of each of the present compounds 1 to 200, and air-drying the thus impregnated base material.

Formulation Example 10
Electric Mosquito Mats

Acetone is added to a mixture of 0.8 g of each of the present compounds 1 to 200 and 0.4 g of piperonyl butoxide to prepare a solution having a total volume of 10 ml. A base material for electric mat (a plate obtained by coagulating fibrils of a mixture of cotton linter and pulp) having an area of 2.5 cm×1.5 cm and a thickness of 0.3 cm is uniformly impregnated with 0.5 ml of the solution prepared above, to obtain an electric mosquito mat.

Formulation Example 11
Electric Mosquito-controlling Devices Using an Insecticidal Solution Electric mosquito-controlling devices using an insecticidal solution of each of the present compounds 1 to 200 are obtained by dissolving 3 parts of each of the present compounds in 97 parts of deodorized kerosene to obtain a solution, placing the solution in a container made of vinyl chloride, and inserting one end of an absorbent wick (obtained by coagulating inorganic powder with a binder and baking the coagulated powder) into the container so that the other end of the wick can be heated with a heater.

Formulation Example 12
Heating Smoking Formulations

Heating smoking formulations of each of the present compounds 1 to 200 are obtained by dissolving 100 mg of each of the present compounds in an adequate amount of acetone to obtain a solution, and impregnating a porous ceramic plate having an area of 4.0 cm square and a thickness of 1.2 mm with the solution.

Formulation Example 13
Poisonous Baits

Ten milligrams of each of the present compounds 1 to 200 is dissolved in 0.5 ml of acetone. The resulting solution is uniformly mixed with 5 g of solid feed powder for animals (solid feed powder for breeding CE-2, a trade name, Oriental Kobo Co.). The resulting mixture is air-dried to remove the acetone, to obtain 0.2% poisonous baits of each of the present compounds.

Formulation Example 14
Acarine-controlling Sheets

Acarine-controlling sheets of each of the present compounds 1 to 200 are obtained by dissolving each of the present compounds in an adequate amount of acetone, impregnating a non-woven fabric with the resulting solution by dropping the solution onto the fabric so that the fabric carries each of the present compounds in an amount of 1 g per square meter, and air-drying the resulting fabric to remove the acetone.

Formulation Example 15
Microcapsules

A mixture of 10 parts of each of the present compound 1 to 200, 10 parts of phenylxylylethane and 0.5 part of Sumidur L-75 (tolylene diisocyanate, mfd. by Sumitomo Bayer Urethane Comp. Ltd.) is added to 20 parts of a 10% aqueous gum arabic solution. The resulting mixture is stirred in a homomixer to obtain an emulsion having an average particle size of 20 $\mu$m. Then, 2 parts of ethylene glycol is added to the emulsion. The resultant mixture is allowed to react on a hot bath at 60° C. for 24 hours to obtain a microcapsule slurry. On the other hand, 0.2 part of xanthan gum and 1.0 part of Veegum R (aluminum magnesium silicate, mfd. by Sanyo Chemical Industries Ltd.) are dispersed in 56.3 parts of ion-exchanged water to obtain a thickening agent solution.

42.5 Parts of the microcapsule slurry prepared above and 57.5 parts of the thickening agent solution prepared above are mixed to obtain 10% microcapsules.

Formulation Example 16
Non-heating Volatile Formulations

Non-heating volatile formulations of each of the present compounds 1 to 200 are obtained by dissolving 100 $\mu$g of each of the present compounds in an adequate amount of acetone, applying the resulting solution uniformly on a filter paper having an area of 2 cm square and a thickness of 0.3 mm, and then air-drying the filter paper to remove the acetone.

The following test examples demonstrate the effectiveness of the present compounds as an active ingredient for pesticidal compositions. In the test examples, the present compounds are identified by the compound numbers shown in Tables 1 to 8.

Test Example 1
Insecticidal Effect on Tobacco Cutworm (*Spodoptera litura*)

Each of the flowable concentrates of the present compounds 9, 11, 15, 34, 36, 40, 10, 20, 24, 35, 49, a 1:1 Mixture of 14 and 39, a 1:1 Mixture of 23 and 48, a 1:1 Mixture of 59 and 84, a 1:1 Mixture of 61 and 86, a 1:1 Mixture of 65 and 90, a 3:2 Mixture of 214 and 239, and, a 3:2 Mixture of 219 and 244, obtained according to Formulation Example 5 was diluted with water so as to have an active ingredient concentration of 500 ppm. With 2 ml of the dilution, 13 g of artificial feed (Insecta LF, mfd. by Nihon Nosan Co.) prepared in a polyethylene cup having a diameter of 11 cm. Five fourth-instar larvae of tobacco cutworm were released in the polyethylene cup. In 6 days, the dead and alive were counted for mortality.

As a result, it was found that the present compounds identified by the following compound numbers had a mortality of 100%: compound Nos. 9, 11, 15, 34, 36, 40, 10, 20, 24, 35, 49, a 1:1 Mixture of 14 and 39, a 1:1 Mixture of 23 and 48, a 1:1 Mixture of 59 and 84, a 1:1 Mixture of 61 and 86, a 1:1 Mixture of 65 and 90, a 3:2 Mixture of 214 and 239, and, a 3:2 Mixture of 219 and 244.

Test Example 2
Insecticidal Effect on Cotton Aphid (*Aphis gossypii*)

At true-leaf planting time, each cucumber plant having a developed first true leaf and planted in a polyethylene cup was inoculated with a piece of cucumber leaf having cotton aphids as parasites. One day after the inoculation, each of flowable concentrates of the present compounds 9, 11, 36, 10, 20, 35, 49, a 1:1 Mixture of 14 and 39, a 1:1 Mixture of 23 and 48, a 1:1 Mixture of 59 and 84, a 1:1 Mixture of 61 and 86, a 1:1 Mixture of 65 and 90, a 3:2 Mixture of 214 and 239, and, a 3:2 Mixture of 219 and 244, obtained according to Formulation Example 5 was diluted with water so as to have an active ingredient concentration of 500 ppm, and the dilution was sprayed in a volume of 20 ml per pot. Six days after the spraying, the control efficacy was calculated by the equation (1):

$$\text{Control efficacy} = \{1-(Cb \times Tai)/(Tb \times Cai)\} \times 100 \quad (1)$$

Cb: Number of insects before spraying in untreated group,
Cai: Number of insects after spraying in untreated group,
Tb: Number of insects before spraying in treated group,
Tai: Number of insects after spraying in treated group.

As a result, it was found that the present compounds identified by the following compound numbers had a control efficacy of 90% or more: compound Nos. 9, 11, 36, 10, 20, 35, 49, a 1:1 Mixture of 14 and 39, a 1:1 Mixture of 23 and 48, a 1:1 Mixture of 59 and 84, a 1:1 Mixture of 61 and 86, a 1:1 Mixture of 65 and 90, a 3:2 Mixture of 214 and 239, and, a 3:2 Mixture of 219 and 244.

Test Example 3
Insecticidal Effect on Housefly (*Musca domestica*)

The bottom of a polyethylene cup having a diameter of 5.5 cm was covered with a filter paper having the same diameter. Each of the flowable concentrates of the present compounds 9, 11, 15, 34, 36, 40, 10, 20, 24, 35, 49, a 1:1 Mixture of 14 and 39, a 1:1 Mixture of 23 and 48, a 1:1 Mixture of 59 and 84, a 1:1 Mixture of 61 and 86, a 1:1 Mixture of 65 and 90, a 3:2 Mixture of 214 and 239, and, a 3:2 Mixture of 219 and 244, respectively, obtained according to Formulation Example 5 was diluted with water so as to have an active ingredient concentration of 500 ppm. 0.7 Milliliter of the dilution was dropped on the filter paper. As diet, 30 mg of sucrose was uniformly placed in the polyethylene cup. Ten female adult houseflies were released in the polyethylene cup and the cup was closed with a lid. In 24 hours, the dead and alive were counted for mortality.

As a result, it was found that the present compounds identified by the following compound numbers had a mortality of 100%: compound Nos. 9, 11, 15, 34, 36, 40, 10, 20, 24, 35, 49, a 1:1 Mixture of 14 and 39, a 1:1 Mixture of 23 and 48, a 1:1 Mixture of 59 and 84, a 1:1 Mixture of 61 and 86, a 1:1 Mixture of 65 and 90, a 3:2 Mixture of 214 and 239, and, a 3:2 Mixture of 219 and 244.

Test Example 4
Insecticidal Effect on German Cockroach (*Blattella germanica*)

The bottom of a polyethylene cup having a diameter of 5.5 cm was covered with a filter paper having the same diameter. Each of the flowable concentrates of the present compounds 9, 11, 15, 34, 36, 40, 10, 20, 24, 35, 49, a 1:1 Mixture of 14 and 39, a 1:1 Mixture of 23 and 48, a 1:1 Mixture of 59 and 84, a 1:1 Mixture of 61 and 86, a 1:1 Mixture of 65 and 90, a 3:2 Mixture of 214 and 239, and, a 3:2 Mixture of 219 and 244, respectively, obtained according to Formulation Example 5 was diluted with water so as to have an active ingredient concentration of 500 ppm. 0.7 Milliliter of the dilution was dropped on the filter paper. As diet, 30 mg of sucrose was uniformly placed in the polyethylene cup. Two male adult German cockroaches were released in the polyethylene cup and the cup was closed with a lid. In 6 days, the dead and alive were counted for mortality.

As a result, it was found that the present compounds identified by the following compound numbers had a mortality of 100%: compound Nos. 9, 11, 15, 34, 36, 40, 10, 20, 24, 35, 49, a 1:1 Mixture of 14 and 39, a 1:1 Mixture of 23 and 48, a 1:1 Mixture of 59 and 84, a 1:1 Mixture of 61 and 86, a 1:1 Mixture of 65 and 90, a 3:2 Mixture of 214 and 239, and, a 3:2 Mixture of 219 and 244.

Test Example 5
Insecticidal Effect on Common Mosquito (*Culex pipiens pallens*)

Each of the flowable concentrates of the present compounds 9, 11, 15, 34, 36, 40, 3, 10, 20, 24, 28, 35, 49, a 1:1 Mixture of 14 and 39, a 1:1 Mixture of 23 and 48, a 1:1 Mixture of 59 and 84, a 1:1 Mixture of 61 and 86, a 1:1 Mixture of 65 and 90, a 3:2 Mixture of 214 and 239, and, a 3:2 Mixture of 219 and 244, respectively, obtained according to Formulation Example 5 was diluted with water so as to have an active ingredient concentration of 500 ppm. 0.7 Milliliter of the dilution was added to 100 ml of ion-exchanged water to adjust the active ingredient concentration to 3.5 ppm. In the resulting solution, 20 final-instar larvae of common mosquito were released. In one day, the dead and alive were counted for mortality.

As a result, it was found that the present compounds identified by the following compound numbers had a mortality of 100%: compound Nos. 9, 11, 15, 34, 36, 40, 3, 10, 20, 24, 28, 35, 49, a 1:1 Mixture of 14 and 39, a 1:1 Mixture of 23 and 48, a 1:1 Mixture of 59 and 84, a 1:1 Mixture of 61 and 86, a 1:1 Mixture of 65 and 90, a 3:2 Mixture of 214 and 239, and, a 3:2 Mixture of 219 and 244.

Test Example 6
Insecticidal Effect on Webbing Clothes Moth (*Tineola bisselliella*) obtained by Vaporization at Ordinary Temperature A 2 cm-square wool clelaine cloth and 10 intermediate-instar larvae of webbing clothes moth were placed in the bottom of a polyethylene cup (diameter of bottom: 10 cm, diameter of mouth: 12.5 cm, height: 9.5 cm, capacity: 950 $cm^3$). Each of the non-heating volatile formulations of the present compounds 11, 36, 9, 10, 34, 35, a 1:1 Mixture of 23 and 48, a 1:1 Mixture of 59 and 84, and, a 1:1 Mixture of 61 and 86, respectively, obtained according to Formulation Example 16 was suspended from the lid of the polyethylene cup, and the cup was sealed up. After standing at a temperature of 25° C. for 1 week, the cup was opened, and the dead, moribund and alive were counted for percentage of moribund or dead larvae. In addition, the degree of vermiculation of the wool delaine cloth was investigated. The degree of vermiculation was decided according to the following criterion:

+++: remarkable vermiculation,

++: considerable vermiculation,

+: some degree of vermiculation,

±: slight vermiculation,

−: no vermiculation.

The same test as above was repeated while replacing the present compounds with, as the reference compounds, each of the compounds disclosed in U.S. Pat. No. 4,219,565, i.e., (2,3,4,5,6-pentachlorophenyl)methyl (1R)-cis-3-(cyclobutoxyiminomethyl)-2,2-dimethylcyclopropanecarboxylate (hereinafter referred to as the reference compound A) and (2,3,4,5,6-pentafluorophenyl)methyl (1R)-trans-3-(cyclopentoxyiminomethyl)-2,2-dimethylcyclopropanecarboxylate (hereinafter referred to as the reference compound B).

Table 17 shows the results.

TABLE 17

| Compound | Percentage of moribund or dead larvae | Degree of vermiculation |
| --- | --- | --- |
| 11 | 100 | − |
| 36 | 100 | − |
| 9 | 100 | + |
| 10 | 100 | − |
| 34 | 90 | + |
| 35 | 100 | − |
| 1:1 Mixture of 23 and 48 | 100 | ± |
| 1:1 Mixture of 59 and 84 | 100 | ± |
| 1:1 Mixture of 61 and 86 | 100 | ± |
| A | 0 | +++ |
| B | 0 | +++ |

Test Example 7

Effect of a Mosquito Coil on Common Mosquito (*Culex pipiens pallens*)

Twenty female adult common mosquitoes were released in a glass chamber (70 cm cube, capacity: 0.34 m$^3$). A piece (0.3 g) was cut off from each of the insecticidal coils of the present compounds 9, 10, 11, 15, 34, 35, 36, 40, 20, 24, 49, a 1:1 Mixture of 61 and 86, a 1:1 Mixture of 23 and 48, a 1:1 Mixture of 59 and 84, and, a 3:2 Mixture of 214 and 239, respectively, which had been prepared according to the process described in Formulation Example 9. The piece was ignited at one end and set vertically on a holder, which was placed in the center of the bottom of the chamber. After 30 seconds of combustion, the piece was taken out of the chamber. Twelve minutes after the setting of the piece, the knocked-down common mosquitoes were counted. The same test as above was repeated while replacing the present compounds with each of the reference compound A and reference compound B used in Test Example 6.

Table 18 shows the results.

TABLE 18

| Compound | Knocked-down |
| --- | --- |
| 9 | 95 |
| 10 | 85 |
| 11 | 100 |
| 15 | 100 |
| 34 | 100 |
| 35 | 100 |
| 36 | 100 |
| 40 | 100 |
| 20 | 100 |
| 24 | 100 |
| 49 | 100 |
| 1:1 Mixture of 61 and 86 | 100 |
| 1:1 Mixture of 23 and 48 | 100 |
| 1:1 Mixture of 59 and 84 | 100 |
| 3:2 Mixture of 214 and 239 | 95 |
| A | 0 |
| B | 30 |

Test Example 8

Effect of Spraying of an Oil Formulation on Housefly (*Musca domestica*)

Twenty adult houseflies (male/female=10/10) wwre released in a glass chamber (70 cm cube, capacity: 0.35 m$^3$). 0.7 Milliliter of each of the oil formulations of the present compounds 9, 10, 11, 15, 34, 35, 36, 40, 20, 24, 49, a 1:1 Mixture of 61 and 86, a 1:1 Mixture of 23 and 48, a 1:1 Mixture of 59 and 84, and, a 3:2 Mixture of 214 and 239, respectively, which had been prepared according to the process described in Formulation Example 6 was sprayed into the chamber with a spray gun at a pressure of 0.9 kg/cm$^2$. Five minutes after the spraying, the knocked-down houseflies were counted.

The same test as above was repeated while replacing the present compounds with each of the reference compound A and reference compound B used in Test Example 7.

Table 19 shows the results.

TABLE 19

| Compound | Knocked-down |
| --- | --- |
| 9 | 90 |
| 10 | 80 |
| 11 | 100 |
| 15 | 80 |
| 34 | 70 |
| 35 | 100 |
| 36 | 95 |
| 40 | 90 |
| 20 | 90 |
| 24 | 80 |
| 49 | 75 |
| 1:1 Mixture of 61 and 86 | 100 |
| 1:1 Mixture of 23 and 48 | 80 |
| 1:1 Mixture of 59 and 84 | 90 |
| 3:2 Mixture of 214 and 239 | 100 |
| A | 0 |
| B | 35 |

The use of the present, compounds provides an excellent pest-controlling effect.

What is claimed is:

1. An ester compound represented by the formula:

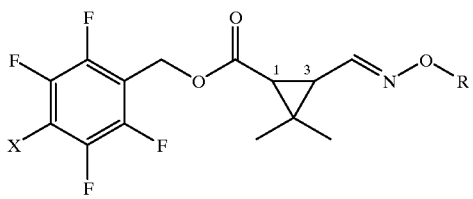

wherein R is a hydrogen atom, a $C_1$–$C_3$ alkyl group unsubstituted or substituted with one or more halogen atoms, an allyl group unsubstituted or substituted with one or more halogen atoms, or a propargyl group unsubstituted or substituted with one or more halogen atoms; and X is a hydrogen atom, a $C_1$–$C_3$ alkyl group unsubstituted or substituted with one or more halogen atoms, a $C_2$–$C_3$ alkenyl group unsubstituted or substituted with one or more halogen atoms, a $C_2$–$C_3$ alkynyl group unsubstituted or substituted with one or more halogen atoms, a $C_1$–$C_3$ alkcoxy group unsubstituted or substituted with one or more halogen atoms, a $C_1$–$C_3$ alkylthio group unsubstituted or substituted with one or more halogen atoms, or a $C_1$–$C_3$ alkoxymethyl group containing a $C_1$–$C_3$ alkoxy group unsubstituted or substituted with one or more halogen atoms.

2. The ester compound according to claim 1, which contains a cyclopropane ring having R-configuration at 1-position.

3. The ester compound according to claim 1, wherein R is a methyl group.

4. The ester compound according to claim 1, wherein X is a hydrogen atom.

5. The ester compound according to claim 1, wherein X is a methyl group.

6. The ester compound according to claim 1, wherein X is a methoxy group.

7. A composition for controlling pests, which comprises an ester compound according to claim 1 as an active ingredient.

8. The ester compound according to claim 1, wherein the substituent in the 1-position of the cyclopropane ring has trans-configuration relative to the substituent in the 3-position of the cyclopropane ring.

9. The ester compound according to claim 1, wherein the substituent in the 1-position of the cyclopropane ring has cis-configuration relative to the substituent in the 3-position of the cyclopropane ring.

10. The ester compound according to claim 2, wherein the substituent in the 1-position of the cyclopropane ring has trans-configuration relative to the substituent in the 3-position of the cyclopropane ring.

11. The ester compound according to claim 2, wherein the substituent in the 1-position of the cyclopropane ring has cis-configuration relative to the substituent in the 3-position of the cyclopropane ring.

12. The ester compound according to claim 1, wherein X is a $C_1$–$C_3$ alkoxy group.

13. The ester compound according to claim 1, wherein X is a $C_1$–$C_3$ alkoxymethyl group.

14. The ester compound according to claim 1, wherein X is a methoxymethyl group.

* * * * *